US006713048B2

United States Patent
Peart et al.

(10) Patent No.: US 6,713,048 B2
(45) Date of Patent: Mar. 30, 2004

(54) $\Delta^9$ TETRAHYDROCANNABINOL ($\Delta^9$ THC) SOLUTION METERED DOSE INHALERS AND METHODS OF USE

(75) Inventors: Joanne Peart, Richmond, VA (US); Peter R. Byron, Richmond, VA (US); Aron H. Lichtman, Richmond, VA (US); Billy R. Martin, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/944,221

(22) Filed: Sep. 4, 2001

(65) Prior Publication Data

US 2002/0031480 A1 Mar. 14, 2002

Related U.S. Application Data

(63) Continuation-in-part of application No. 09/273,766, filed on Mar. 22, 1999, now Pat. No. 6,509,005
(60) Provisional application No. 60/105,850, filed on Oct. 27, 1998.

(51) Int. Cl.[7] .......................... A61L 9/04; A01N 43/16; A61K 31/35

(52) U.S. Cl. ........................................ 424/45; 514/454

(58) Field of Search .............................. 424/43, 45, 46; 514/454

(56) References Cited

U.S. PATENT DOCUMENTS

| | | | |
|---|---|---|---|
| 4,087,546 A | * 5/1978 | Archer et al. | 424/283 |
| 4,087,547 A | * 5/1978 | Archer et al. | 424/283 |
| 4,464,378 A | * 8/1984 | Hussain | 424/260 |
| 4,476,140 A | * 10/1984 | Sears et al. | 424/283 |
| 4,635,651 A | * 1/1987 | Jacobs | 131/270 |
| 4,847,290 A | * 7/1989 | Burstein | 514/454 |
| 5,492,688 A | 2/1996 | Byron et al. | |
| 5,502,076 A | * 3/1996 | Dixit et al. | 514/510 |
| 5,538,993 A | * 7/1996 | Mechoulam et al. | 514/454 |
| 5,653,961 A | * 8/1997 | McNally et al. | 424/45 |
| 5,683,676 A | * 11/1997 | Akehurst et al. | 424/45 |
| 5,736,124 A | * 4/1998 | Akehurst et al. | 424/45 |
| 5,776,433 A | * 7/1998 | Tzou et al. | 424/45 |
| 5,804,592 A | * 9/1998 | Volicer | 514/454 |
| 5,916,540 A | * 6/1999 | Akehurst et al. | 424/45 |
| 5,922,306 A | * 7/1999 | Akehurst et al. | 424/45 |
| 5,976,574 A | * 11/1999 | Gordon | 424/489 |
| 5,980,867 A | * 11/1999 | Tzou et al. | 424/45 |
| 5,981,572 A | * 11/1999 | Ellis et al. | 514/456 |
| 5,985,248 A | * 11/1999 | Gordon et al. | 424/46 |
| 6,001,336 A | * 12/1999 | Gordon | 424/46 |
| 6,017,963 A | * 1/2000 | Alfonso et al. | 514/646 |
| 6,039,932 A | * 3/2000 | Govind et al. | 424/45 |

OTHER PUBLICATIONS

Bliss, C.I. (1967). Statistics in Biology; New York; McGraw–Hill; pp 439. No date.
Gill, E.W., et al.; Blood and Brain Levels of Delta1–tetrahydrocannibinol in mice—The effect of 7–hydroxy–delta1–tetrahydrocannabinol; Biochemical Pharmacology, vol. 23, pp 1140–1143, 1974.
Ross, S., et al.; Constituents of Cannabis Sativa L. XXXVIII; A Review of the Natural Constituents: 1980–1994; Zagazig J Pharm Sci, Dec., 1995; vol. 4, No. 2, pp. 1–10.
Tashkin, DP, et al., Subacute Effects of Heavy Marihuana Smoking on Pulmonary Function in Healthy Men; New Eng. J of Med. 294:125–129, Jan. 15, 1976.
Turner, et al., Constituents of Cannabis sativa L. XVIII—Electron Voltage Selected Ion Monitoring Study of Cannabinoids; Biomedical Mass Spectrometry, vol., 7, No. 6, 1990 pp. 247–256.
Maurer et al.; Delta9 tetrahydrocannabinol Shows Antispastic and Analgesic Effects in a Single Case Double–blind Trial; Eur Arch Psychiatry Clin Neurosci 240:1–4, 1990.
Workshop on the medical utility of marijuana. National Institutes of Health, Aug. 1997.
Olsen, J.L., Lodge, J.W., Shapiro, B.J. and Tashkin, D.P. (1976). An inhalation of $\Delta^9$–tetrahydrocannabinol. *Journal of Pharmacy and Pharmacology*, 28:86.
Thornton, Jacqul, (Jun. 13, 1999). Cannabis inhalers in first legal health test. *Electronic Telegraph, UK News Summary*, www.telegraphco.UK, Issue 1479.
Tashkin, D.P., Reiss, S., Shapiro, B.J., Calvarese, B., Olsen, J.L. and Lodge, J.W. (1977). Bronchial effects of aerosolized $\Delta^9$–tetrahydrocannabinol in healthy and asthmatic subjects. *American Review of Respiratory Disease*. 115:57–65.
Williams, S.J., Hartley, J.P.R., Graham, J.D.P. (1976). Bronchodilator effect$\Delta^1$–tetrahydrocannabinol administered by aerosol to asthmatic patients. *Thorax*. 31:720–723.
Long–Term Efficacy and Safety of Dronabinol for Aquired Immunodeficiency Syndrome–Associated Anorexia, Journal of Pain and Symptom Management; vol. 14 No. 1 Jul. 1997 pp. 7–14.
Dronabinol as a Treatment for Anorexia Associated with Weight Loss in Patients with AIDS; Journal of Pain and Symptom Management; vol. 10 No . 2; Feb. 1995; pp. 89–97.

(List continued on next page.)

Primary Examiner—Sreeni Padmanabhan
Assistant Examiner—Lauren Q. Wells
(74) Attorney, Agent, or Firm—Whitham, Curtis & Christofferson, P.C.

(57) ABSTRACT

The present invention provides therapeutic formulations for solutions of $\Delta^9$-tetrahydrocannabinol ($\Delta^9$ THC) to be delivered by metered dose inhalers. The formulations, which use, non-CFC propellants, provide a stable aerosol-deliverable source of $\Delta^9$ THC for the treatment of various medical conditions, such as: nausea and vomiting associated with chemotherapy-muscle spasticity; pain; anorexia associated with AIDS wasting syndrome, epilepsy; glaucoma; bronchial asthma; and mood disorders.

16 Claims, 8 Drawing Sheets

OTHER PUBLICATIONS

Efficacy of tetrahydrocannabinol in patients refactory to standard antiemetic therapy; Investigational New Drugs 6:243–246; (1988); Mary McCabe, Frederick P. Smith, John S. Macdonald, Paul V. Woolley, Deborah Goldberg, and Philip S. Schien; Divisional of Medical Oncology, Vincent T. Lombardi Cancer Research Center, Dept. of Medicine. Georgetown University.

Tetrahydrocannabinol for Refractory Vomiting Induced by Cancer Chemotherapy; JAMA Mar. 28, 1980–vol 243, No. 12.

Antiemetics–Sallan, et al. The New England Journal of Medicine; Jan. 17, 1980; vol 302 No. 3; pp. 135–138.

Delta–9–Tetrahydrocannabinol as an Antiemetic for Patients rceiving Cancer Chemotherapy; Dec. 1979; Annals of Internal Medicine; vol 91 No. 6; pp. 825–830.

Delta–9–Tetrahydrocannabinol as an Antiemetic in Cancer Patients Receiving High–Dose Methotrexate; Dec. 1979; Annals of Internal Medicine; vol. 91 No. 6; pp. 820–824.

Analgesic effect of Delta–9–tetrahydrocannabinol; Dept. of Psychiatry and Internal Medicine, University of Iowa College; Feb.–Mar. 1975; pp. 139–143.

Analgesic Properties of delta–9–tetrahydrocannabinol and codiene; Depart., of Psychiatry and Medicine, University of Iowa; published Mar. 29, 1975; pp. 84–89.

The effect of orally rectally administered 9–tetrahydrocannabinol on spasticity: A pilot study with 2 patients, Institute of Pharmacy, University of Bern; International Journal of Clinical Pharmacology and Therapeutics, vol. 34 No. 10–1996 (446–452).

Delta–9–THC in the Treatment of Spasticity Associated with Multiple Sclerosis; Dept. of Psychiatry at U.C.L.A; 1988 Hawthorne Press; pp. 39–50.

Tetrahydrocannabinol for Tremor in Multiple Sclerosis; David Clifford, MD; Division of Clinical Neuropharmacology and Dept. fo Neurology and Neurological Surgery Washington School fo Medicine, Published Dec. 12, 1982; Annals of Neurology vol. 13 No. 6 Jun. 1983; pp. 669–671.

Treatment of Human Spasticity with 9–Tetrahydrocannabinol; J. Clin Pharmacol. 1981:21:413S–416S.

Delta–9–tetrahydrocannbinol shows antipastic and anaglesic effects in a single case double–blind trial; Eur Arch Psychiatry Clin Neurosci 1990:240(1):1–4.

Effect of Marihuana on Intraocular and Blood Pressure in Glaucoma; American Academy of Ophthalmology; Mar. 1980 vol. 87 No. 3; pp. 222–228.

Effect of Delta–9–Tetrahydrocannabinol on Intracular Pressure in Humans; Aug. 1977; Southern Medical Journal vol., 70 No. 8; pp. 951–954.

Antiemetic Effect of Delta–9–Tetrahydrocannabinol in patients receiving Cancer Chemotherapy; New England Journal of Medicine; Oct. 16, 1975, vol. 293 No. 16 pp. 795–797.

Comparison of output particle Size Distributions from Pressurized Aerosols Formulated as Solutions or Suspensions; Pharmaceutical Rsearch vol. 5 No. 1, 1988, Plenum Publishing Corp. pp. 36–39.

Changing to CFC–Free Inhalers: The Technical and Clinical challenges; The Pharmaceutical Journal vol. 259; Nov. 29, 1997; pp. 896–898.

Drug–surfactant–propellant interactions in HFA–formulations; Internatinal Journal of Pharmaceutics; 186 (1999) 13–30.

Drug form Selection in Albuterol–containing Metered–Dose Inhaler Formulations and its Impact on Chemical and Physical Stability; Journal of Pharmaceuticals Sciences; vol. 86 No. 12, Dec. 1997 pp. 1352–1357.

The Identification, isolation, and preservation of 9–tetrahydrocannabional Dept. Of Toxicology, Indiana University Med. Ctr., J. Pharm. 1971, 23, 190–195.

Stability of Tetrahydrocannabinols IJ. Pharmceuticals Sciences vol. 63, No. 10., Oct. 1974; pp. 1563–1574.

Asgharian, B., Wood, r. & Schlesinger, R.B. (1995). Empirical modeling of particle deposition in the alveolar region of the lungs: A basis for interspecies extrapolation. Fund Appl toxicol, 27, 232–238.

Barnett, C., Chiang, C., Perez–Reyes, M. & Owens, S. (1982). Kinetic study of smoking marijuana. J. Pharmacokin Biopharm, 10, 495–506.

Byron, P.R. (1994) Dosing reproducibility from experimental albuterol suspension metered–dose inhalers. Pharm Res, 11, 580–4.

Chiang, C.W. & Barnett, G. (1984). Marijuana effect and delta–9–tetrahydrocannabinol plasma level. Clin Pharmacol Ther, 36–234–238.

Christensen, H.d., Freudenthal, R.I., Gidley, J.T., Rosenfeld, R., Boegli, G., Testino, L., Brine, D.R., Pitt, C.G., & Wall, M.E., (1971) Activity of Delta8–and Delta–9–tetrahydrocannabinol and related compounds in the mouse. Science, 172, 165–167.

Compton, D., Aceto, M., Lowe, J. & Martin, B. (1996) In vivo characterization of a specific cannabinoid receptor antagonist (SR141716A): inhibition of delta 9–tetrahydrocannabinol–induced responses and apparent agonist activity. J. Pharmacol Exp. Ther, 277,586–594.

Compton, D.R., Rice, K.C., De Costa, B.R., Razdan, R.K., Melvin, L.S., Johnson, M.R. & Marin, B.R. (1993). Cannabinoid structure–activity relationships: Correlation of receptor binding and in vivo activities. J. Pharmacol Exp Ther, 265, 218–226.

Cone, E. & Huestis, M., (1993). Relating blood concentrations of tetrahydrocannabinol and metabolites to phamacologic effects and time of marihuana usage. Ther Drug Mon, 15, 527–532.

D'Amour, F.E. & Smith, D.L. (1941) A method for determining loss of pain sensation. J. Pharm Exp Ther, 72, 74–79.

Ford, R.D., Balster, R.L., Dewey, W.L., & Beckner, J.S., (1977). Delta 9–THC and 11–OH–delta 9–THC: Behavioral effects and relationship to plasma and brain levels. Life Sci., 20, 1993–20004.

Gill, E. W. & Jones, J. (1972) Brain levels of delta 1–tetrahydrocannabinol and its metabolites in mice–correlation with behavior, and the effect of the metabolic inhibitors SKF 525A and piperonyl butoxide. Biochem. Pharmacol., 21, 2237–2248.

Gupta, P.K. & Hickey, A.J. (1991). Contemporay approaches in aerosolized drig delivery to the lungs. J. Controlled release, 17, 129–148.

Henderson, R., Tennant, F., & Guerney, R. (1972) Respitory manifestations of hashish smoking. Arch Otol, 95,248–251.

Hiller, F.C., Wison, F.J.J., Mazumder, M.K., Wison, J.D. & Bone, R.C., (1984) Concentration and particle size distribution in smoke from marijuana cigarettes with different delta 9–tetrahydrocannabinol content. Fundam Appl Toxicol, 4,451–454.

House-of-Lords-Select-Committee-on-Science-and-Technology (1998). Ninth Report. Cnnabis: The Scientific and Medical Evidence.

Huber, G.L., Simmons, G.A., McCarthy, C.R., Cutting, MB., Laguarda, R. & Pereira, W. (1975) Depressant effect of marijuana smoke on antibactercidal activity of pulmonary alveolar macrophages. Chest, 68, 769–73.

Huestis, M.A., Sampson, A.H., Holicky, B.J., Henningfield, J.E. & Cone, E.J. (1992) Characterization of the absorption phase of marijuana smoking. Clin Pharmacol Ther, 52, 31–41.

Johansson, E., Ohlsson, A., Lindgren, J.E., Agurell, S., Gillespies, H. & Hollister, L.E. (1987) Single-dose kinetics of deuterium-labelled cannabinol in man after intravenous adminsitration and smoking. Biomed Envirom Mass Spectrum, 14, 495–499.

Lichtman, A.H., Poklis, J.L., Poklis, A., Wilson, D.M. & Martin, B.R. (2001) The pharmacological activity of inhalation exposure to maijuana smoke in mice. Drug Alc Depend 63,107–116.

Little, P.J., Compton, D.r., Johnson. MR., Melvin, L.S. & Martin, B.R. )1988) Phamrmacology and stereoselectivity of structally novel cannabinoids in mice J. Phaarmacol Exp Ther, 247, 745–747.

Mattes, R.D., Shaw, L.M., Edling–Owens, J., Engleman, K. & Elsohly, M.A. (1993) Bypassing the first-pass effect for the therapeutic use of cannabinoids. Pharmacol Biochem Behav, 44, 745–747.

Matthias, P., Tashkin, DP., Marques–Magallnes, J.A., Wilkins, J.N. & Simmons, M.S. (1997) Effects of Varying Marijuana Potency on Depositionof Tar and Delta 9–THC in the Lung During Smoking. Pharmacol Biochem Behav. 58, 1145–1150.

Ohlsson, A., Lindgren, J.E., Wahlem, A., Agurell, S., Hollister, L. E. & gillespie, H.K. (1980) Plasma delta–9 tetrahydrocannabinol concentrations and clinical effects after oral and intravenous administration and smokin. Clin Pharmacol Ther, 28, 409–16.

Ohlsson, A., M. Widman, M., Carlsson, S., Ryman, t., & Strid, C. (1980) Plasma and brain levels of delta 6–THC and seven monooxygenated metabolites correlated to the cataleptic effect in the mouse. Acta Pharmacol. Et Toxicol., 47, 308–317.

Perlin, E., Smith, C.G., Nichols, A.I., Almirez, r., Flora, K.P., Cradock, J.C. & Peck, C.C. (1985) Disposition and bioavailability of various fourmulations of tetrahydrocannabinol in the rhesus monkey,. J. Pharm Sci, 74, 171–174.

rinaldi–Carmona, M., Barth, F., Heaulme, M., Shire, D., Calandra, B., Congy, C., Martinez, S., Maruani, J., Neliat, G., Caput, D., Ferrara, P., Soubrie, P., Breliere, J.C., & Lefur, G. (1994) SR141716A, a potent and selective antagonist of the brain cannabinoid receptor. GEBS Lett, 350, 240–244.

Schlesinger, R.B. (1985) Comparative deposition of inhaled aerosols in experimental animals and humans a review. J. Toxical Environ Health, 15, 197–214.

USP (2000) Physical Tests and Determinations. <601> Aersols, metered-dose inhalers, and dry powder inhalers. In United States Pharmacopeia (USP 24) pp. 1895–1912. Philadelphia, PA: National Publishing.

Vachon, L., Robins, A. & Gaensler, E.A. (1976) Airways response to aerosolized delta 9-tetrahydrocannabinol: preliminary report. In The Therapeutic potential of marijuana. Ed. Cohem, S. & Stillman, R.C. pp. 111–121. New York: Plenum Medical Book Company.

Vaswani, S.K. & Crticos, P.S. (1998) Metered dose inhaler: past, present, and future. Ann Allergy Asthma Innuol, 80, 11–9; quiz 19–20.

T. Tzou, Density, Excess Molar Volume, and Vapor Pressure of Propellant Mixtures in metered–Dose Inhalers: Deviation from Ideal Mixtures; T. Tzou; Respiratory Drug Delivery, VI, 1998 439–443.

J. H. Bell, et al.; Variation in delivery of isoprenaline from variuos pressurizedinhalers, J. Pharm. Pharmac., 1973, Suppl. 32P–36P.

J. H. Bell, et al.; Variation in delivery of isoprenaline from variuos pressurizedinhalers, J Pharm. Pharmac, 1973, Suppl. 32P–36P.

P. Moren; Drug Deposition of pressurized inhalation aerosols Influence of vapour pressure and metered volume; Int'l Journal of Pharmaceuticals,1 (1978) 213–218.

* cited by examiner

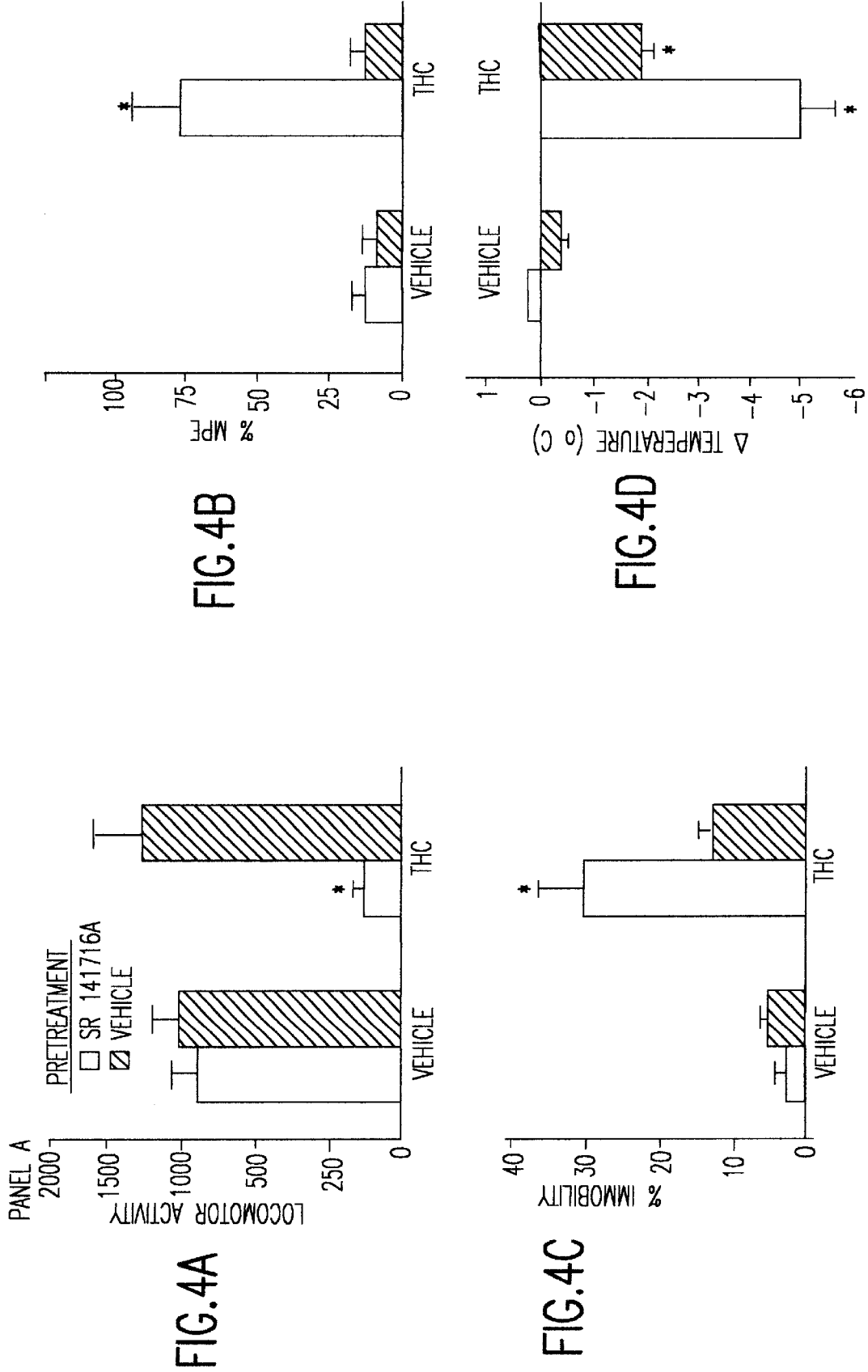

HFA 134A

HFA 227

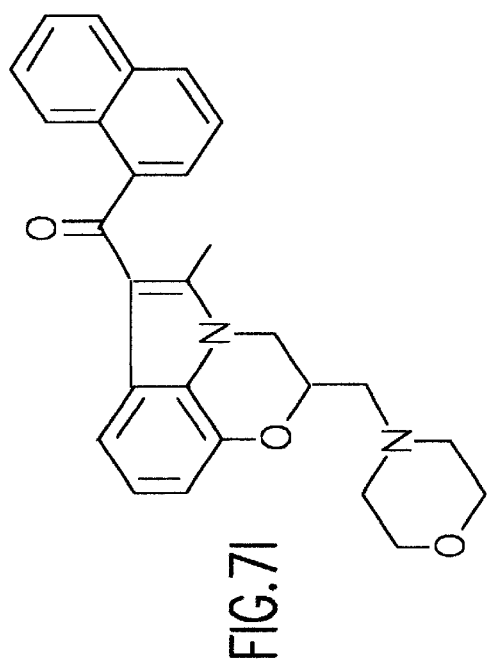
FIG.7G
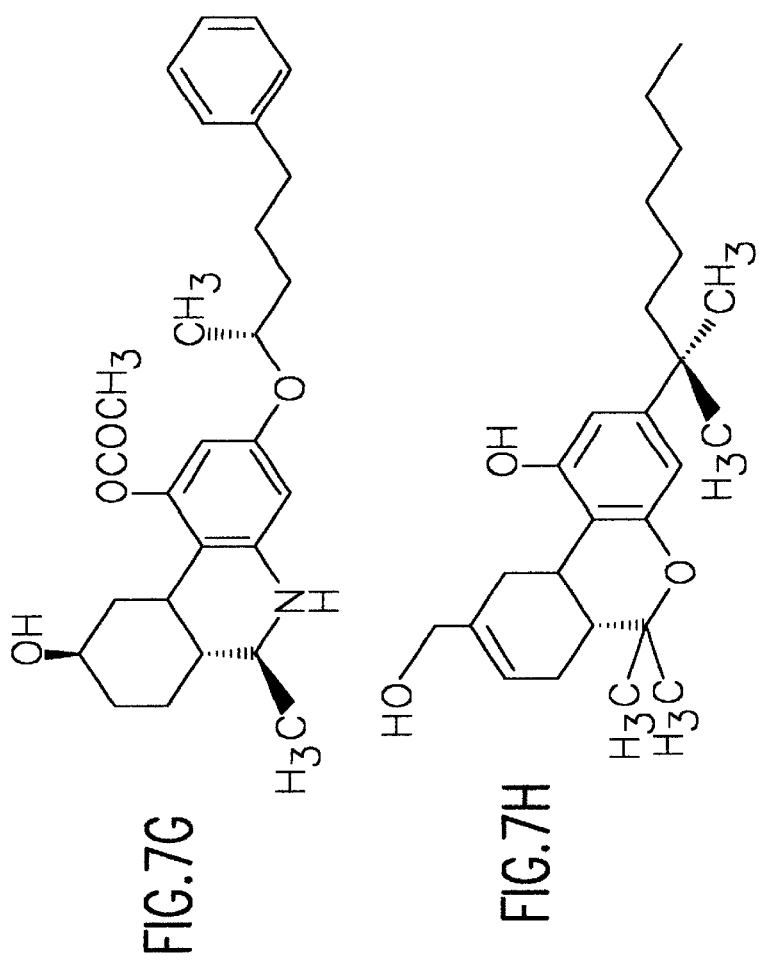
FIG.7H
FIG.7I
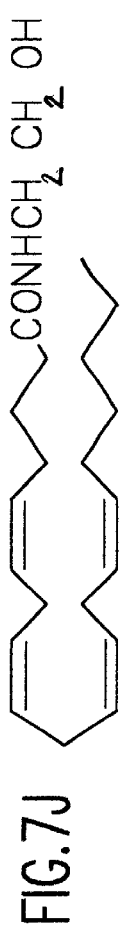
FIG.7J
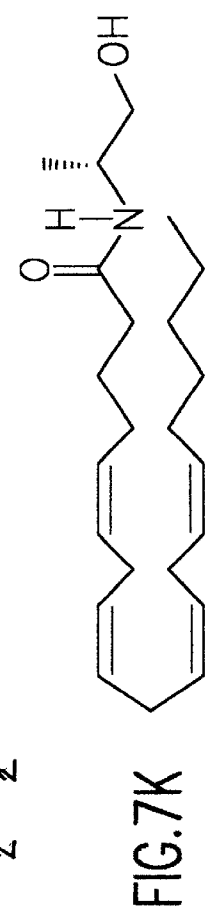
FIG.7K

$\Delta^9$ TETRAHYDROCANNABINOL ($\Delta^9$ THC) SOLUTION METERED DOSE INHALERS AND METHODS OF USE

CROSS REFERENCE TO RELATED APPLICATIONS

This application is a continuation-in-part of U.S. Ser. No. 09/273,766 filed Mar. 22, 1999, now U.S. Pat. No. 6,509,005 which claims priority of U.S. provisional application Ser. No. 60/105,850 filed October 27, 1998, and the complete contents of those applications are incorporated herein by reference.

Funding for the research which led to this invention was provided in part by the United States Government in grant #DA 02396 and DA-07027 from the National Institutes of Health and the government may have certain rights in this invention.

BACKGROUND OF THE INVENTION

1. Field of the Invention

The invention is generally related to the therapeutic use of $\Delta^9$ Tetrahydrocannabinol ($\Delta^9$ THC). In particular, the invention provides a metered dose inhaler (MDI) for the aerosol administration of $\Delta^9$ THC to patients suffering from nausea and vomiting associated with cancer chemotherapy, muscle spasticity, pain, anorexia associated with AIDS wasting syndrome, epilepsy, glaucoma, bronchial asthma, mood disorders, and the like.

2. Background Description

In 1997, the National Institutes of Health (NIH) released a review of the scientific data concerning potential therapeutic uses for marijuana. In that review, the NIH found that marijuana may indeed have beneficial medicinal effects and recommended that researchers develop alternative dosage forms for the drug, such as a "smoke free" inhaled delivery system. Workshop on the medical utility of marijuana, National Institutes of Health, August 1997. Studies have documented therapeutically beneficial medicinal uses of the major active component of marijuana, $\Delta^9$ tetrahydrocannabinol ($\Delta^9$ THC). Beal, J. A., Olson, R., Lefkowitz, L., Laubenstein, L., Bellman, P., Yangco, B., Morales, J. O., Murphy, R., Powderly, W., Plasse,.T. F., Mosdell, K. W. and Shepard, K. W., Long-term efficacy and safety of dronabinol for acquired immnunodeficiency syndrome-associated anorexia, J Pain. Symptom Manage. 14:7–14 (1997); Beal, J. A., Olson, R., Laubenstein, L., Morales, J. O., Beliman, B., Yangco, B., Lefkowitz, L., Plasse, T. F. and Shepard, K. V. Dronabinol as a treatment for anorexia associated with weight loss in patients with AIDS, J Pain. Symptom Manage,. 10:89–97 (1995); McCabe, M., Smith, F. P., MacDonald, J. S., Wooley, P. V., Goldberg, D. and Schein, P. S., Efficacy of tetrahydrocannabinol in patients refractory to standard antiemetic therapy, Invest. New Drugs 6:243–246 (1988); Lucas, V. S. and Laszlo, J. $\Delta^9$-THC for refractory vomiting induced by cancer chemotherapy, JAMA 243:1241–1243 (1980); Sallan, S. E., Cronin, C., Zelen, M. and Zinberg, N. E., Antiemetics in patients receiving chemotherapy for cancer: a randomized comparison of $\Delta^9$ THC and prochlorperazine, N. Engl. J Med., 302:135–138 (1980); Frytak, S., Moertel, C. G., O'Fallon, J R., Rubin, J., Creagan, E.T., O'Connell, M. J., Schutt, A. J. and Schwartau, N. W., Delta-9-tetrahydrocannabinol as an antiemetic for patients receiving cancer chemotherapy: a comparison with prochlorperazine and a placebo, Ann. Inter. Med 91:825–830 (1979); Chang, A. E., Shiling, D. J., Stillman, R. C., Goldgerg, N. H., Seipp, C.A., Barofdky, I., Simon, R. M. and Rosenberg S A, $\Delta^9$ THC as an antiemitic in cancer patients receiving high-dose methotrexate. Ann. Internal Med. 91:819–824 (1979); Sallan, S. E., Zinberg, N. E. and Frei, I.E., Antiemetic effect of $\Delta^9$ THC in patients receiving cancer chemotherapy, New Engl. J Med. 293:795–797 (1975); Noyes, J R., Brunk, S. F., Baram, D. A. and Canter, A., The analgesic properties of $\Delta^9$ THC and codeine. J Clin. Pharmacol 15:139–143 (1975); Noyes, R., Jr., Brunk, S. F., Baram, D. A. and Canter, A., Analgesic effect of $\Delta^9$ tetrahydrocannabinol, Clin. Pharmacol & Ther 18:84–89 (1975); Brenneisen, R., Egli, A., Elosohlly, M. A., Henn, V. and Spiess, Y., The effect of orally and rectally administered $\Delta^9$ THC on spasticity: a pilot study with 2 patients, Int. J Clin. J Pharmocol Ther. 34:446–452 (1996); Ungerleider, J. T., Andyrsiak, T. F. L., Ellison, G. W. and Myers, L. W., $\Delta^9$ THC in the treatment of spasticity associated with multiple sclerosis, Adv. Alcohol Subst. Abuse 7:39–50 (1987); Clifford, D. B., Tetra-hydrocannabinol for tremor in multiple sclerosis, Ann. Neurol 13:669–171 (1983); Petro, D. J. and Ellenberger, C., Treatment of human spasticity with delta 9 -tetrahydrocannabinol, J Clin. Pharmacol 21:413S–416S (1981); Maurer, M., Henn, V., Dittrich, A. and Hofman, A., Delta 9-tetrahydrocannabinol shows antispastic and analgesic effects in a single case double-blind trial, Eur. Arch. Psychiatry Neurol Sci. 240:1–4 (1990); Merritt, J., Crawford, W., Alexander, P., Anduze, A. and Gelbart, S., Effects of marijuana on intra ocular and blood pressure in glaucoma, Opht. 87:222–228 (1980); Cooler, P. and Gregg, J. M., Effect of delta 9-$\Delta^9$ THC on intra ocular pressure in humans. South. Med J 70:951–954 (1977). Table 1 summarizes the findings of these studies.

TABLE 1

The Use of $\Delta^9$ THC for the Treatment of Assorted Clinical Conditions

| Condition and Number of Patients | Administration Route and Dose | Findings | Reference |
|---|---|---|---|
| AIDS-associated anorexia and cachexia; 94 patients; 12 months | Oral placebo, 2.5 mg THC once or twice daily increasing to 20 mg daily | Long term THC treatment was well-tolerated; THC improved appetite and only tended to increase weight compared to controls | Beal et al., 1997 |
| AIDS-associated anorexia and cachexia; 139 patients; 42 days | Oral placebo or 2.5 mg THC twice daily | 57% and 69% of vehicle and THC patients were evaluable for efficacy. Appetite increased 38% over baseline for THC group compared to only | Beal et al., 1995 |

TABLE 1-continued

The Use of $\Delta^9$ THC for the Treatment of Assorted Clinical Conditions

| Condition and Number of Patients | Administration Route and Dose | Findings | Reference |
|---|---|---|---|
| | | 8% for the placebo group. THC also decreased nausea. No significant changes were found between the groups for weight change. | |
| Nausea and emesis due to Cancer chemotherapy; 36 patients who had experienced severe nausea and vomiting that was refractory to prochlorperazine or thiethylperazine | Oral THC, 15 mg/m² | Reduction in chemotherapy-induced nausea and vomiting in 64% of patients given THC compared to prochloperazine; side effects included dysphoria; authors recommend initial THC dose of 5 mg/m² | McCabe et al., 1988 |
| Nausea and emesis due to Cancer chemotherapy; 53 patients which were refractory to other antiemetics | Oral 5 or 15 mg/m² THC four times per day | 72% of patients exhibited a THC-induced partial or complete blockade of vomiting | Lucas and Laszlo, 1980 |
| Nausea and emesis due to cancer chemotherapy; 84 patients | Oral 10 mg/m² THC of prochloperazine | THC more effective than prochloperazine | Sallan et al., 1980 |
| Nausea and emesis due to Cancer chemotherapy; 116 patients | Oral 15 mg THC, 10 mg prochloperzine or placebo | Equal antiemetic effects between THC and prochlorperazine, effects of each greater than placebo; considerately more CNS side effects with THC than prochlorperazine | Frytak et al., 1979 |
| Nausea and emesis due to Cancer chemotherapy; 15 patients | Oral placebo or 10 mg/m² THC every 3 hours for a total of 5 doses, THC (17 mg) laced cigarettes of placebo were given if vomiting occurred | 93% patients had a reduction in nausea and vomiting, 53% had an excellent response, 40% had a fair response; plasma THC levels 7.1 ± 6.9 (mean + SD) ng/ml. Side effects tachycardia, few other side effects | Chang et al., 1979 |
| Pain due to advanced cancer; 10 patients | Oral placebo and 5, 10, 15 or 20 mg THC | Pain relief, elevated mood, appetite stimulation, drowsiness, slurred speech, mental clouding | Noyes, et al., 1975 |
| Pain due to advanced cancer; 34 patients | Placebo, 10 and 20 mg THC, and 60 and 120 codeine | THC produced a similar degree of analgesia, with greater potency than codeine. THC CNS side effects included sedation, mental clouding, ataxia, and disorientation | Noyes et al., 1975 |
| Spasticity related to multiple sclerosis; 2 patients | Oral 10 or 15 mg THC, rectal dose of 5 or 10 mg THC | Improvement in passive mobility and walking ability | Brenneisen et al., 1996 |
| Spasticity related to multiple sclerosis; 13 patients | Oral 2.5 to 15 mg THC once or twice daily or placebo | Significant subjective improvement in spasticity at 7.5 mg THC and higher, no significant improvement in objective measurements | Ungerleider et al., 1987 |
| Spasticity related to multiple sclerosis; 8 patients, single blind | Oral 5 to 15 mg THC | 5 of 8 patients had mild subjective improvement in tremor. 2 of 8 patients had both objective and subjective improvement | Clifford, 1983 |
| Spasticity related to multiple sclerosis; 9 patients | Placebo, or 5 or 10 mg THC | Decrease in spasticity compared to placebo treatment, minimal side effects | Petro and Ellenberger, 1981 |
| Spasticity and pain due to spinal cord injury; 1 patient | Oral placebo, THC (5 mg), or codeine (50 mg) | THC and codeine had analgesic effect compared to the placebo treatment. THC had a beneficial effect on spasticity whereas codeine did not | Maurer et al., 1990 |

TABLE 1-continued

The Use of Δ⁹ THC for the Treatment of Assorted Clinical Conditions

| Condition and Number of Patients | Administration Route and Dose | Findings | Reference |
|---|---|---|---|
| Glaucoma, 6 patients | Oral placebo or 5, 10, 15 and 20 mg THC | Pain relief, elevated mood, appetite stimulation, drowsiness, slurred speech, mental clouding | Merritt et al, 1980 |
| Ten subjects with normal intra ocular pressure | Intravenous THC (0.022 or 0.044 mg/kg) | Decreased intra ocular presser by mean of 37% | Cooler and Gregg, 1977 |
| Nausea and emesis due to cancer chemotherapy; refractory to other antiemetics | Oral 10 mg/m² THC or placebo | In 20 courses of THC, 5 resulted in no vomiting, 9 resulted in a reduction of vomiting, 3 resulted in no decrease in vomiting, and 2 were unevaluable. THC was significantly better than placebo in decreasing vomiting | Sallan et al., 1975 |

The year after the 1997 NIH study, the House of Lords made a recommendation to the British government (House-of-Lords-Select-Committee-on-Science-and-Technology, 1998) to reschedule marijuana. Similarly, there have been efforts to decriminalize marijuana in the United States.

When marijuana is used as a recreational psychoactive drug, the active ingredient Δ⁹ THC is usually delivered to the lungs as an impure non-pharmaceutical aerosol in the form of marijuana smoke. Aerosolized Δ⁹ THC in the inhaled smoke is absorbed within seconds and delivered to the brain efficiently. The pharmacokinetics of the administration of Δ⁹ THC is described in PDR Physician's Desk Reference (49) Montvalek, New Jersey: Medical Economics Data Production Co. (1995), pp.2787; Ohlsson, A., Lindgren J. E., Wahlen, A., Agurall, S., Hollister, L. E. and Gillespie, H. K., Plasma Δ⁹ THC concentrations and effects after oral and intravenous administration and smoking, *Clin. Phamacol Ther.* 28:409–416 (1980), summarized in Table 2 below. As can be seen, inhalation is the preferred route of delivery for Δ⁹ THC. When compared to oral delivery, inhalation provides a more rapid onset of pharmacological action and peak plasma levels. The effects achieved via inhalation are comparable to those achieved when the drug is administered intravenously, but inhalation is a much less invasive technique.

Currently, the sources of Δ⁹ THC for patients who could benefit from the drug are limited. An oral form of Δ⁹ THC (MARINOL) is marketed as a treatment for nausea and vomiting related to cancer chemotherapy, and as an appetite stimulant in patients suffering from AIDS wasting syndrome. In MARINOL, pharmaceutical grade Δ⁹ THC is dissolved in sesame oil, encapsulated in gelatin capsules and delivered orally. However, when the drug is taken orally, the absorption is slower and more variable than when inhaled, with an onset of action between 30 minutes and 2 hours (Table 2). Drawbacks of MARINOL include its slow onset of action and extensive first-pass metabolism (Mattes, R. D. Shaw, L. M., Edling-Owens, J., Engelman, K., Elsohly, M. A., Bypassing the first-pass effect for the therapeutic use of cannabinoids, *Pharmacol Biochem Behav*, 44:745–747 (1993); Ohlsson, Lindgren, Whlen, Agurell, Hollister, Gillespie, Plasma delta-9-hydrocannabinol concentration and clinical effects after oral and intravenous administration and smoking, *Clin Pharmacol Ther* (1980), supra; PDR, 2000; Perlin, E., Smith, C. G., Nichols, A. I., Almirez, R., Flora, K. P., Cradock, J. C., Peck, C.C., Disposition and bioavailability of various formulations of tetrahydrocannabinol in the rhesus monkey, *J Pharm Sci*, 74:171–174 (1985)). There is also the difficulty of taking an oral medication during nausea and vomiting.

In contrast, inhalation of marijuana smoke (as some cancer patients do to alleviate nausea and vomiting due to

TABLE 2

Pharmacokinetics of Δ⁹ THC Given Orally, Intravenously or by Smoking

| Route | Dose | % Dose in Plasma | Onset of Pharmacological Action | Peak Plasma Levels | References |
|---|---|---|---|---|---|
| Oral, sesame oil in gelatin capsules | 2.5, 5, or 10 mg | 10 to 20% | 0.5 to 1 hour | 120–480 min | (PDR, 1995) |
| Oral, in cookies | 20 mg | 4 to 12% | 120–180 min | 60–90 min | (Ohlsson, et al., 1980) |
| Intravenous, bolus | 5 mg | 100% | 10 min | 3 min | (Ohlsson, et al., 1980) |
| Smoking (THC lost to side stream smoke and pyrolysis | 13 mg | 8 to 24% | 10 min | 3 min | (Ohlsson, et al., 1980) | chemotherapy) results in the rapid delivery of a systemic dose of $\Delta^9$ THC while avoiding the first-pass metabolism. Barnett C., Chiang, C., Perez-Reyes, M., Owens, S., Kinetic study of smoking marijuana, *J Pharmacokin Biopharm*, 10, 495–506 (1982); Chiang, C. W., Barnett, G., Marijuana effect and delta-9-tetrahydrocannabinol plasma level, *Clin Pharmacolo Ther*, 36,234–238 (1984); Cone, E., Huestis, M., Relating blood concentrations of tetrahydrocannabinol and metabolites to Few pharmacologic effects and time of marijuana usage, *Ther Drug Mon*, 15:527–532 (1993); Huestis, M. A., Sampson, A. H., Holicky, B. J., Henningfield, J. E., Cone, E. J., Characterization of the absorption phase of marijuana smoking, *Clin Pharmacol Ther*, 52:31–41 (1992); Johansson, E., Ohlsson, A., Lindgren, J. E., Agurell, S., Gillespie, H., Hollister, L. E., Single-dose kinetics of deuterium-labelled cannabinol in man after intravenous administration and smoking, *Biomed Environ Mass Spectrom*, 14:495–499 (1987); Ohlsson, A., Lindgren, J. E., Wahlen, A., Agurell, S., Hollister, L. E., Gillespie, H. K., Plasma delta-9 tetrahydrocannabinol concentrations and clinical effects after oral and intravenous administration and smoking, *Clin Pharmacol Ther*, 28:409–16 (1980). Thus a patient would be expected to have better control by using the smoking route than from an orally administered gel capsule. However, inhalation of marijuana smoke exposes the user to mutagens, carcinogens, and other harmful by-products of pyrolysis. Hiller, F. C., Wilson, F. J. J., Mazumder, M. K., Wilson, J. D., Bone, R. C., Concentration and particle size distribution in smoke from marijuana cigarettes with different $\Delta^9$-tetrahydrocannabinol content, *Fundam Appl Toxicol*, 4:451–454 (1984); Matthias, P., Tashkin, D. P., Marques-Magallanes, J. A., Wilkins, J. N., Simmons, M. S., Effects of Varying Marijuana Potency on Deposition of Tar and $\Delta^9$-THC in the Lung During Smoking, *Pharmacol Biochem Behav*, 58:1145–1150 (1997). In heavy users, marijuana smoke causes bronchial irritation and impaired airway conductance (Henderson, R., Tennant, F., Guemey, R., Respiratory manifestations of hashish smoking, *Arch Otol*, 95:248–251 (1972); Tashkin, D., Shapiro, B., Lee, Y., Harper, C., Subacute effects of heavy marijuana smoking on pulmonary function in healthy men, *N Eng J Med*, 294:125–129 (1976)), as well as depressed alveoloar macrophage bactericidal activity (Huber, G. L., Simmons, G. A., McCarthy, C. R., Cutting, M. B., Laguarda, R., Pereira, W., Depressant effect of marijuana smoke on anti-bactericidal activity of pulmonary alveolar macrophages, *Chest*, 68:769–73 (1975)). Another concern is the presence of numerous untested chemicals in the smoke. In addition to $\Delta^9$ THC, marijuana contains at least 60 cannabinoids and over 400 total chemical constituents (Ross, S., Elsohyl, M., Constituents of *Cannabis saliva L.*, XXVIII, A review of the natural constituents: 1980–1984, *Zagazig J Pharm Sci*, 4:1–10 (1995); Turner, C., Bouwsma, O., Billets, S., Elsohly, M., Constituents of *Cannabis saliva L.* XCIII—Electron voltage selected ion monitoring study in cannabinoids, *Biomed Mass Spectrom*, 7:247–256 (1980)), increasing the likelihood of multiple drug interactions. Further, marijuana remains illegal in most jurisdictions. Inhalation of marijuana smoke is thus not a particularly desirable treatment.

The Institute of Medicine (IOM) recently reviewed the scientific evidence for the potential of marijuana and its cannabinoid constituents to act as therapeutic agents. Joy, J., Watson Jr., S., Benson, J. E., Marijuana and Medicine: Assessing the Science Base (Washington, D.C.: National Academy Press, 1999). This report concluded that there is a potential for cannabinoid drugs, mainly $\Delta^9$ THC, for alleviation of pain, control of nausea and vomiting, and stimulation of appetite. However, they pointed out that marijuana is a "crude $\Delta^9$—THC delivery system" that delivers harmful chemicals along with the delivery of $\Delta^9$ THC, and recommended instead the development of a rapid-onset, reliable, and safe delivery $\Delta^9$ THC system. The House of Lords Select Committee on Science and Technology (Ninth Report) made similar suggestions to the British Government (House-of-Lords-Select-Committee-on-Science-and-Technology, 1998). Although the scheduling of cannabis has not been changed by the British or U.S. governments, the U.S. FDA has rescheduled MARINOL to a Schedule 3 drug, thus increasing the feasibility of developing other delivery forms of the drug.

There is no currently available pharmaceutically acceptable aerosol form of $\Delta^9$ THC. It would be advantageous to have available a form of pharmaceutical grade $\Delta^9$ THC that could be administered as an aerosol. This would provide a means for rapid uptake of the drug. Also, the potential adverse side effects encountered by smoking marijuana would be avoided. Further, an aerosol preparation of pharmaceutically pure $\Delta^9$ THC could be administered in known, controlled dosages. In 1976, Olsen et al. described a chlorofluorocarbon (CFC) propelled MDI formulation of $\Delta^9$ THC. Olsen, J. L., Lodge, J. W., Shapiro, B. J. and Tashkin, D. P. ,An inhalation aerosol of $\Delta^9$-tetrahydrocannabinol. *J Pharmacy and pharmacol.*, 28:86 (1976). However, $\Delta^9$ THC is known to deteriorate during storage, and the stability of $\Delta^9$ THC in this formulation is suspect. In addition, the ethanol content in this formulation was so high (~23%) as to create an aerosol with droplets too large to be effectively inhaled. Dalby, R.N. and Byron, P. R., Comparison of output particle size distributions from pressurized aerosols formulated as solutions or suspensions, *Pharm. Res.* 5:36–39 (1988). The $\Delta^9$ THC CFC formulations were tested for use in treating asthma but were shown to be only moderately effective. Tashkin, D. P., Reiss, S., Shapiro, B. J., Calvarese, B., Olsen, J. L. and Lidgek, J. W., Bronchial effects of aerosolized $\Delta^9$-tetrahydrocannabinol in healthy and asthmatic subjects, *Amer. Rev. of Resp. Disease*. 115.:57–65 (1977); Williams, S. J., Hartley, J. P. R. and Graham, J. D. P., Bronchodilator effect of delta-9-THC administered by aerosol to asthmatic patients. *Thorax*. 31:720–723 (1976). Moreover, CFC propellants have since been banned so that a CFC propellant alternative would be particularly useful. It would clearly be advantageous to develop new aerosol formulations using a non-CFC propellant and having other advantageous features.

To date, much of the $\Delta^9$-THC aerosol exposure in humans concentrates on the bronchodilation effects of $\Delta^9$-THC. Tashkin et al. (1977) used a $\Delta^9$-THC MDI to deliver aerosolized $\Delta^9$-THC to healthy and asthmatic patients in an effort to assess bronchodilation as well as possible side effects due to systemic absorption. Tashkin, D. P., Reiss, S., Shapiro, B. J., Calvarese, B., Olsen, J. L., Lodge, J. W., Bronchial effects of aerosolized delta-9-tetrahydrocannabinol in healthy and asthmatic subjects, *Am Rev Respir Dis*, 115:57–65 (1977). In healthy patients, bronchodilation was seen, as well as substantial systemic side effects (increased heart rate and subjective reports of being 'high') at higher doses. However, in some asthmatic patients, bronchoconstriction occurred. Tashkin et al. suggested that large particle size of the $\Delta^9$-THC aerosol may have caused the local irritant effects. Vachon et al. (1976) reported the use of a nebulized $\Delta^9$-THC micro-aerosol to achieve bronchodilation without systemic effects, however, the propylene glycol vehicle had irritant effects. Vachon, J., Robins, A., Gaensler, E. A., Airways, response to aerosolized delta-9-tetrahydrocannabinol: preliminary report, in *The therapeutic potential of marijuana*, eds. Cohen, S., Stillman, R.C., pp. 111–121 (New York: Plenum Medical Book Co., 1976). Williams et al. (1976) also used a low concentration of $\Delta^9$-THC for bronchodilation without systemic side effects or detectable levels of $\Delta^9$-THC in the blood. Williams, S. J., Hartley, J. P., Graham, J. D., Bronchodilator effect of delta$^1$-tetrahydrocannabinol administered by aerosol of asthmatic patients, *Thorax*, 6:720–723 (1976). It would clearly be advantageous to develop new aerosol formulations in which the $\Delta^9$ THC is stable, the droplets are of a size that can be effectively inhaled, and which use a non-CFC propellant.

Such objectives have been long desired but difficult to achieve, because of problems such as the difficulty of working with $\Delta^9$ THC, large dosage amounts required for $\Delta^9$ THC, and properties of $\Delta^9$ THC that make it unlike, and not interchangeable with, most other drugs. For example, $\Delta^9$ THC resembles rubber-cement, rather than a powder like most drugs, and thus presents formulation difficulties. Scientists working with THC found that they had to go to great lengths to combat its instability, based on its instability to light, oxygen, acids, bases, metal ions, etc. Thus, after the initial interest in the 1970s in THC/CFC aerosols, scientists generally settled into an acceptance of the unworkability of a THC aerosol. The initial promise of a THC aerosol according to J. L. Olsen, J. W. Lodge, B. J. Shapiro and D. P. Tashkin (1975) never materialized, and in the past few decades it has been conventionally thought that THC is not suited for aerosol-dispensing, and especially not for MDI-dispensing.

Thus, a pharmaceutically effective THC aerosol that overcomes the above-mentioned limitations of the prior art, especially an MDI-dispensible aerosol would be much desired.

SUMMARY OF THE INVENTION

The present inventors have now discovered, surprisingly, that THC dissolves well in HFA and that an aerosol-dispensable THC/HFA, pharmaceutical composition—i.e., a sufficiently stable composition and at the high doses which are required for THC—may be formulated. The present invention exploits these surprising discoveries. It is an object of the present invention to provide a stable aerosol-dispensable pharmaceutical composition comprising a non-CFC propellant and a pharmaceutically effective concentration of $\Delta^9$ THC, and $\Delta^9$ THC derivatives (e.g., cannabinoids such as $\Delta^8$-tetrahydrocannabinol, 11-hydroxy $\Delta^9$-tetrahydrocannabinol, cannabinol, cannabidol, nabilone, levonantradol, (–)-HU-210, Win 55212–2, Anandamide, Methandamide, CP 55940, O-1057, SR141716A, etc.). More particularly, it is an object of the present invention to provide a stable aerosol-dispensable pharmaceutical composition comprising a hydrofluoroalkane propellant (for example, HFA 227 or HFA 134a) and $\Delta^9$ THC. The propellant is present in the range of approximately 78 to 100% by weight, and more particularly the propellant is present in the range of approximately 85 to 100% by weight. An organic solvent such as ethanol can be used to assist in solubilizing the $\Delta^9$ THC in the propellant but is not required. If a solvent is used, preferably less than 20% by weight will be required, and most preferably less than 15% by weight will be required. The pharmaceutically effective concentration of $\Delta^9$ THC is preferably in the range of 0.05 to 10% by weight, and most preferably in the range of 0.1 to 6% by weight. The pharmaceutical composition of the present invention can be used to treat a variety of medical conditions including nausea and vomiting associated with cancer chemotherapy, muscle spasticity, pain, anorexia associated with AIDS wasting syndrome, anorexia associated with cancer chemotherapy, epilepsy, glaucoma, bronchial asthma, mood disorders, migraine headaches.

DETAILED DESCRIPTION OF THE DRAWINGS

FIGS. 4A–D are graphs showing the effect of pretreatment with SR 141716A on the behavioral effects of inhaled $\Delta^9$-THC according to the invention for mice.

Figure 5:
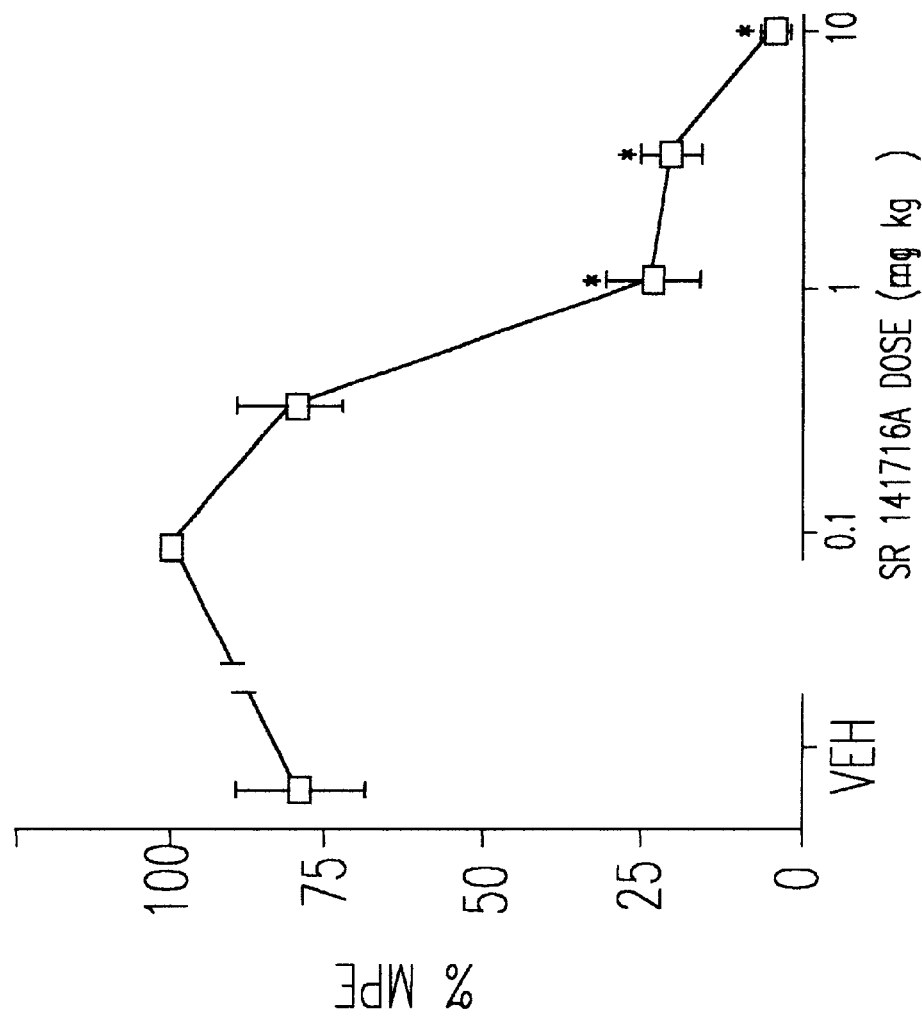

FIG. 5 is a graph of % MPE versus SR 141716A dose, showing the dose-response relationship of SR 141716A in antagonizing the antinociceptive effects following exposure to aerosolized $\Delta^9$-THC according to the invention.

Figure 6A:
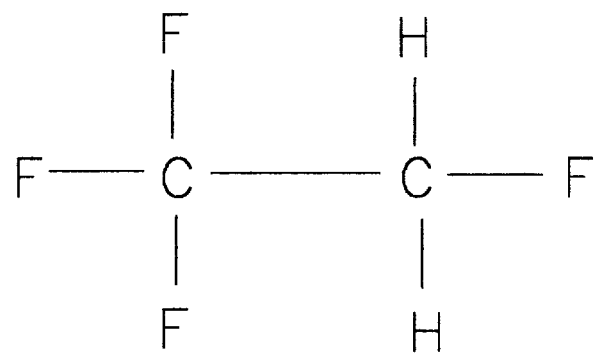
Figure 6B:
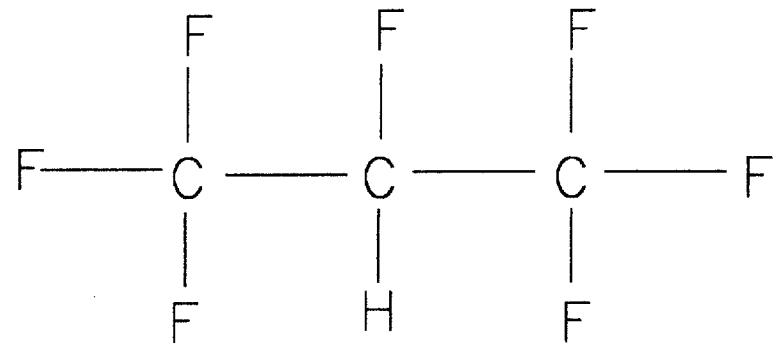

FIG. 6A is the chemical structure for HFA 134a; FIG. 6B is the chemical structure for HFA 227.

Figure 7A:
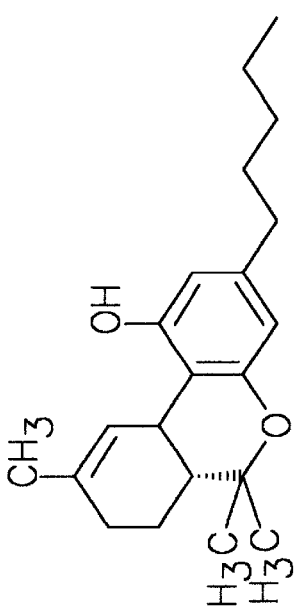
Figure 7B:
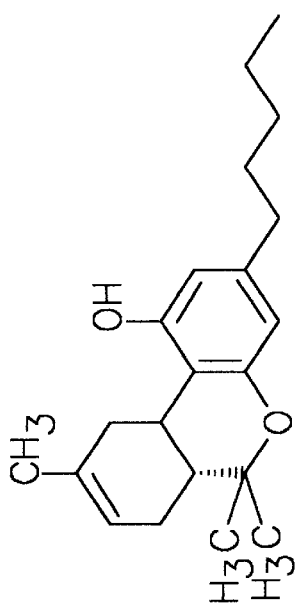
Figure 7C:
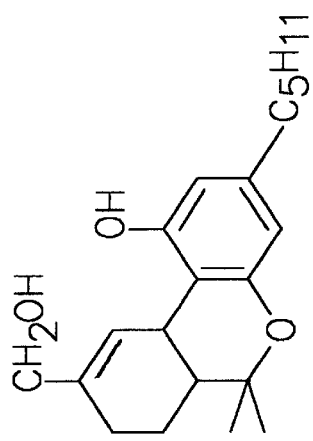
Figure 7D:
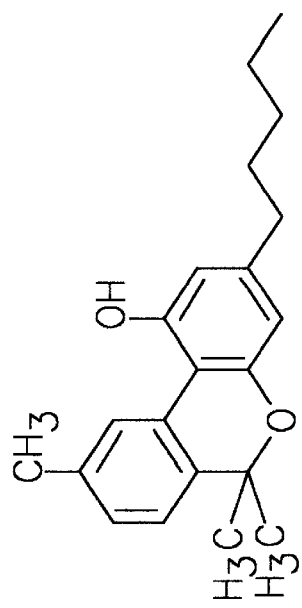
Figure 7E:
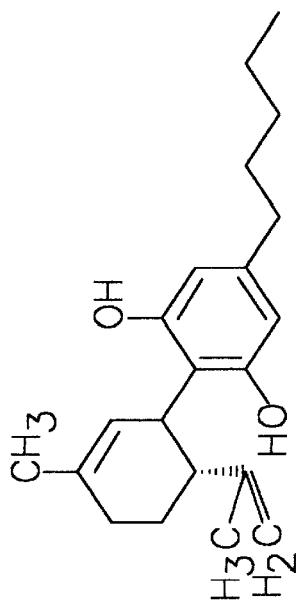
Figure 7F:
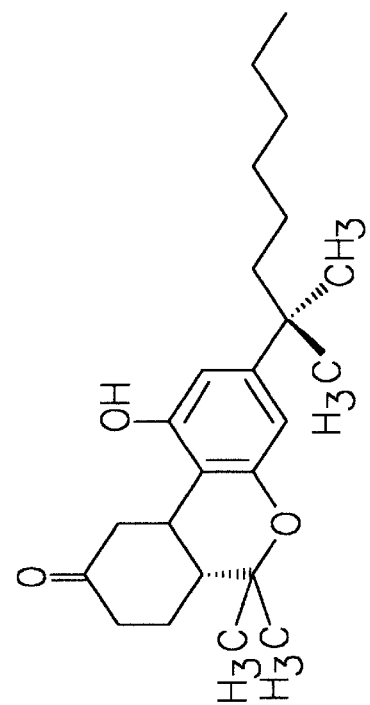
Figure 7L:
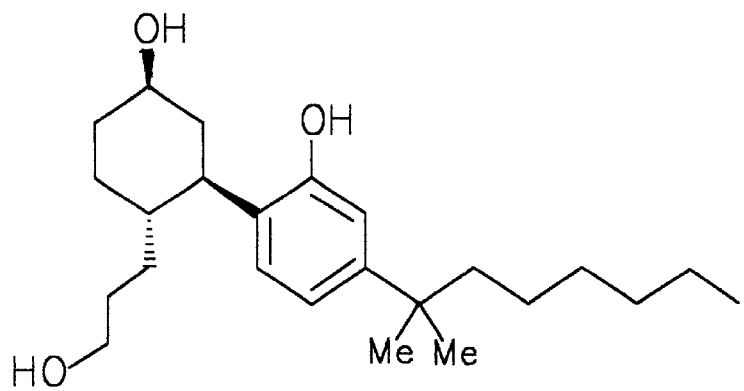
Figure 7M:
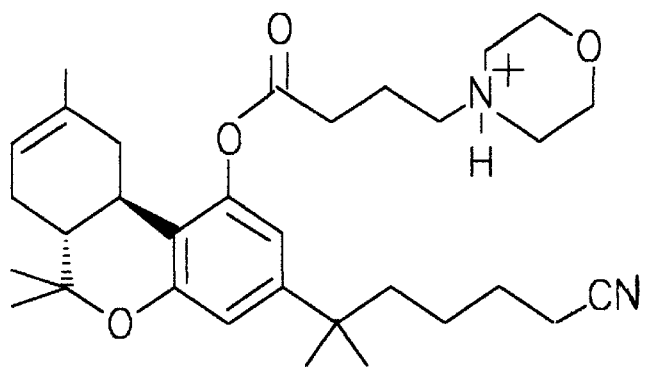
Figure 7N:
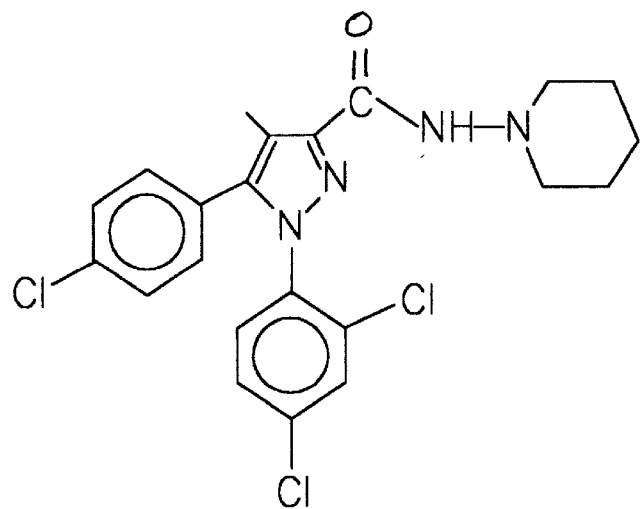

FIG. 7A is the chemical formula for $\Delta^9$ THC and FIGS. 7B–7N are chemical formulae for compounds according to the present invention, including $\Delta^8$ THC (FIG. 7B), 11 hydroxy $\Delta^9$-THC (FIG. 7C), cannabinol (CBN) (FIG. 7D), cannabidiol (CBD) (FIG. 7E), nabilone (FIG. 7F), levonantradol (FIG. 7G), (–)-HU-210 (FIG. 7H), Win 55212-2 (FIG. 7I) Anandamide (FIG. 7J), Methandamide (FIG. 7K), CP 55940 (FIG. 7L), O-1057 (FIG. 7M) and SR141716A (FIG. 7N).

DETAILED DESCRIPTION OF A PREFERRED EMBODIMENT OF THE INVENTION

The instant invention provides non-ozone depleting pressurized metered dose inhaler formulations of $\Delta^9$ THC. In preferred embodiments of the invention, the formulations contain the pharmaceutically acceptable, non-ozone depleting hydrofluoroalkane propellants HFA 134a (1,1,1,2-tetrafluoroethane) and HFA 227 (1,1,1,2,3,3,3-heptafluoropropane), or a mixture thereof.

When the propellant is a hydrofluoroalkane, it has been discovered that the propellant may be used with or without a solvent such as ethanol. Higher percentages of solvent generally allow higher levels of dissolution of $\Delta^9$ THC. However, higher percentages of solvent also cause droplet size to increase. In preferred embodiments of the invention, the range of propellant compositions, as shown in Table 3, may be from 100% propellant and 0% solvent to 85% propellant and 15% solvent. Within this range of percentages, pharmaceutically useful concentrations of $\Delta^9$ THC can be achieved and droplet size is still small enough (<5.8 um) to provide excellent aerosol delivery of the drug. While these ratios reflect preferred embodiments of the invention, it will be recognized by those of skill in the art that the exact ratio of propellant to solvent (e.g. ethanol) may vary according to the desired final concentration of $\Delta^9$ THC and droplet size. Any ratio of propellant to solvent that results in appropriate sized droplets and adequate dissolution of the $\Delta^9$ THC may be used in the practice of this invention, and this will generally be in the range of from 100 to 80% propellant and 0 to 20% solvent. It is expected that a wide variety of solvents, such as ethanol, propanol, propylene glycol, glycerol, polyethylene glycol, etc. may be used in the preparation of formulations contemplated by this invention.

Those skilled in the art also will recognize that the "respirable dose" (or mass of $\Delta^9$ THC in particles with aerodynamic diameters small enough to be delivered to and absorbed by the lungs) (FIG. 1) may be increased by choosing MDI spray nozzles of different design and smaller orifice diameters. Respirable doses may also be increased by extending the mouthpiece of the MDI in such a way as to create an integral or separate aerosol spacer or reservoir attached to the mouthpiece of the MDI. This promotes an increase in droplet evaporation and hence in the percentage of the dose in smaller "respirable" particles or droplets. Generally, the optimal size of a respirable droplet is less than 10 micrometers ($\mu$m) in size. The size of a droplet in an aerosol may be measured by cascade impaction and is characterized by the mass median aerodynamic diameter (MMAD) (the value for which 50% of the particles are larger or smaller). Using THC aerosols according to the present invention, an MMAD of 2.5 $\mu$m or better may be provided.

valve lubrication, the useful life of the MDI and its ability to deliver an accurate dose of drug are severely attenuated. However, probably due to the inherent lubricity of the formulations of the present invention, the use of such surface active agents is unnecessary. This simplifies the composition and thus is an advantage with respect to cost and the elimination of potentially deleterious interactions between components of the formulations and the agents.

A major consideration in the formulation of any drug is its stability. $\Delta^9$ THC is known to deteriorate upon storage so that the effective concentration decreases and the purity is vitiated. The stability of the formulations of the present invention were tested according to accelerated storage testing protocols. The results are given in FIG. 1 and Tables 4A and 4B. The formulations of the present invention were shown to be stable with respect to the release of aerosolized $\Delta^9$ THC in reproducible doses following accelerated storage testing. Apparently, the containment of $\Delta^9$ THC in solution in the non-aqueous formulations of the present invention is excellent with respect to chemical degration, making possible the construction of a multidose inhaler with a good shelf life prognosis.

TABLE 3

Apparent Solubility of $\Delta^9$ THC in Ethanol/HFA Propellant Blends

| Formulation | Mass (g) of $\Delta^9$ THC in Sample | Mass (g) of Formulation Sampled | Apparent Solubility Mean (±SD) | Comments |
|---|---|---|---|---|
| $\Delta^9$ THC in 100% HFA 134a | 0.000240 | 0.1071 | 0.224% w/w (±0.063) | Excess $\Delta^9$ THC added to propellant blend (in pressurized MDI). Solubility sample removed using puff absorber n = 5 |
| $\Delta^9$ THC in 5% Ethanol/95% HFA 134a | 0.00144 | 0.0914 | 1.585% w/w (±0.321) | As above |
| $\Delta^9$ THC in 10% Ethanol/90% HPA 134a | 0.00363 | 0.1036 | 3.511 % w/w (±0.249) | As above |
| $\Delta^9$ THC in 15% Ethanol/85% HFA 134a | 0.00536 | 0.1098 | 4.883% w/w (±0.224) | As above |
| $\Delta^9$ THC in 100% HFA 227 | 0.00021 | 0.1451 | 0.147% w/w (±0.008) | As above |
| $\Delta^9$ THC in 5% Ethanol/95% HFA 227 | 0.00134 | 0.0979 (±0.169) | 1.339% w/w | As above |
| $\Delta^9$ THC in 10% Ethanol/90% HFA 227 | 0.00454 | 0.1267 | 3.240% w/w (±0.161) | As above |
| $\Delta^9$ THC in 15% Ethanol/85% HFA 227 | 0.00623 | 0.1062 | 5.940% w/w (±0.191) | As above |

A distinct advantage of the present formulations is that, surprisingly, the use of surface active agents or "surfactants" as valve lubricants and solubilizers is not necessary. This is in contrast to the invention of Purewal and Greenleaf (European Patent 0,372,777 (Riker Laboratories), Medicinal aerosol formulations) which provides HFA 134a/ethanol mixtures to produce stable formulations of pharmaceuticals in the presence of lipophilic surface active agents. Lipophilic surface active agents are incorporated in that invention in order to suspend undissolved material and to ensure adequate valve lubrication of the MDI. Without adequate Further, lipophilic materials like $\Delta^9$ THC are generally known to partition into the elastomers of the valves in MDI formulations. ($\Delta^9$ THC is highly lipophilic as reflected in its octanol:water partition coefficient of 6000:1). Over time, this partitioning results in a decrease in the emitted or delivered dose of a liophilic drug. Thus, this phenomenon also decreases the useful shelf-life of such preparations. However, the data presented in FIG. 1 and Table 4 show that this is not the case with the formulations of the present invention. The emitted or delivered doses were constant over the time period tested. This may be due to the somewhat surprising preference of $\Delta^9$ THC for the formulation itself; rather than for the valve elastomers.

ranged from 0.147% w/w to 5.94%. w/w as the propellant composition varied from 100% HFA 227 to 85% HFA 227

TABLE 4A

Formulation and aerosol characteristics of $\Delta^9$ THC pressurized metered dose inhalers in ethanol/hydrofluoroalkane (HFA) propellant blends.

| | Formulation (% (w/w)) | | | |
|---|---|---|---|---|
| Inhaler | $\Delta^9$ THC | Ethanol | Propellant | Description |
| 1 | 0.13% | ~5% | 95% HFA 134a | 3/98 Pale Yellow Solution |
| 2 | 0.13% | ~5% | 95% HFA 227 | 3/98 Pale Yellow Solution |
| 3 | 0.12% | ~5% | 95% HFA 134a | 3/98 Pale Yellow Solution |
| 4 | 0.18% | ~5% | 95% HFA 134a | 3/98 Pale Yellow Solution |
| 5 | 0.27% | ~5% | 95% HFA 227 | 3/98 Pale Yellow Solution |
| 6 | 0.25% | ~5% | 95% HFA 134a | 3/98 Pale Yellow Solution |
| 7 | 0.57% | ~5% | 95% HFA 134a | 3/98 Yellow Solution |
| 8 | 0.58% | ~5% | 95% HFA 227 | 3/98 Yellow Solution |
| 9 | 0.49% | ~5% | 95% HFA 134a | 3/98 Yellow Solution |
| 10 | 1.02% | ~5% | 95% HFA 134a | 3/98 Yellow Solution |
| 11 | 1.11% | ~5% | 95% HFA 227 | 3/98 Yellow Solution |
| 12 | 0.97% | ~5% | 95% HFA 134a | 3/98 Yellow Solution |
| SS* #1 Initial | 1.07% | 4.94% | 94.0% HFA 134a | 6/98 Yellow Solution |
| SS* #1 after 28 days at 40° C./82% RH** | 1.07% | 4.94% | 94.0% HFA 134a | 7/98 Yellow Solution |
| SS* #2 after 21 days at 40° C./82% RH** | 1.00% | 5.01% | 94% HFA 134a | 7/98 Yellow Solution |
| SS* #3 Modified Actuator*** | 1.02% | 5.15% | 93.8% HFA 134a | 10/98 Yellow Solution |

[a]Mean (Standard Deviation) of five determinations.
[b]Mass of $\Delta^9$ THC aerosol particles < 5.8 μm aerodynamic diameter
*SS: Stability Sample
**RH: relative humidity
***Approximate spray nozzle diameter = 0.2 mm.

TABLE 4B

Formulation and aerosol characteristics of $\Delta^9$ THC pressurized metered dose inhalers in ethanol/hydrofluoroalkane (HFA) propellant blends.

| | Aerosol Characterization | | |
|---|---|---|---|
| Inhaler | Metered Dose (mg)[a] | Emitted Dose (mg)[a] | Fine Particle Dose (mg)[a,b] |
| 11 | 1.72 (0.25) | 1.32 (0.17) | ND |
| 12 | 0.94 (0.23) | 0.97 (0.10) | 0.38 (0.02) |
| SS* #1 Initial | 1.10 (0.07) | 0.90 (0.03) | 0.22 (0.03) |
| SS* #1 after 28 days at 40° C./82% RH** | 1.06 (0.03) | 0.92 (0.04) | 0.23 (0.02) |
| SS* #2 after 21 days at 40° C./82% RH** | 1.02 (0.05) | 0.90 (0.05) | 0.21 (0.02) |
| SS #3 Modified Actuator*** | ND | ND | 0.40 (n = 1) |

[a]Mean (Standard Deviation) of five determinations.
[b]Mass of $\Delta^9$ THC aerosol particles < 5.8 μm aerodynamic diameter
*SS: Stability Sample
**RH: relative humidity
***Approximate spray nozzle diameter = 0.2 mm
ND: not determined The final concentration of $\Delta^9$ THC in a given formulation may be varied by adjusting the ratio of propellant to solvent and thus the solubility of the $\Delta^9$ THC. Higher percentages of solvent (e.g. ethanol) generally allow a higher amount of $\Delta^9$ THC to be dissolved. For example, in preferred embodiments of the invention, the apparent solubility of $\Delta^9$ THC and 15% ethanol. Thus, the dose of $\Delta^9$ THC in a given metered volume may be selected by changing the formulation.

Figure 1:
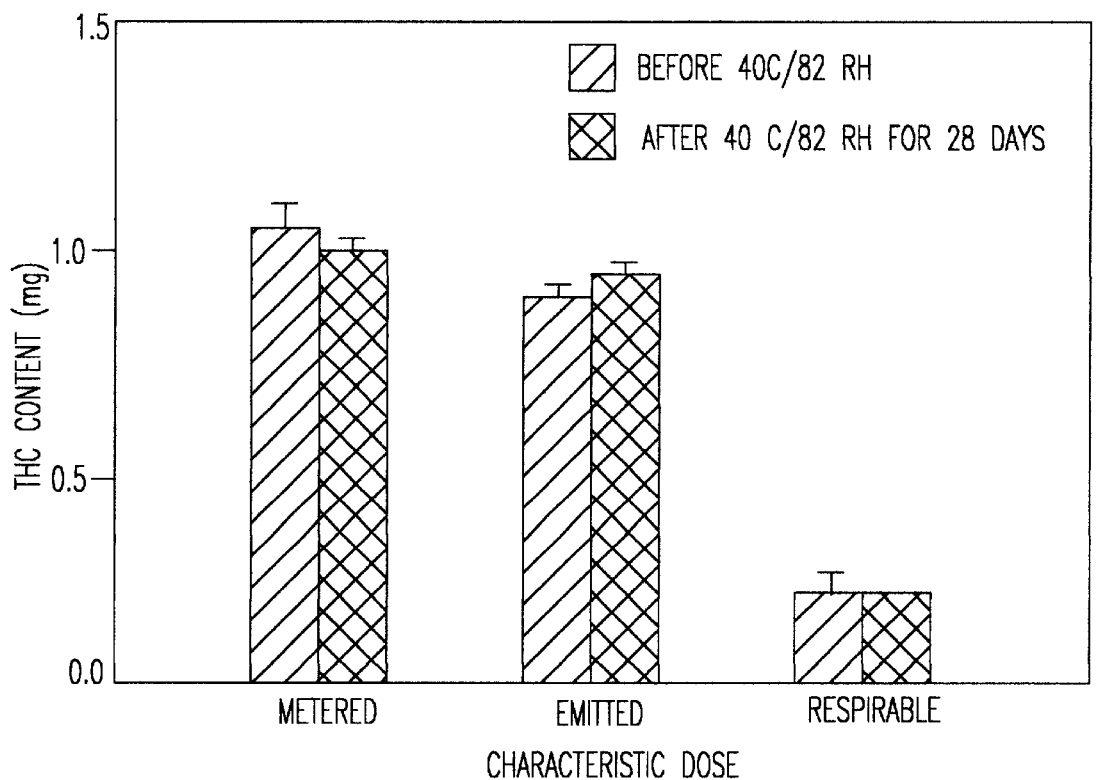
FIG. 1 is a $\Delta^9$ THC MDI characterization summary before and after storage at 40° C. and 82% relative humidity (RH).

Further, as stated above, the "fine particle dose" or "respirable dose" of a drug dispensed with an MDI is a function of the spray nozzle diameter. In FIG. 1 and Tables 4A and 4B, the spray nozzle diameter is 0.4 mm. The "fine particle dose" or "respirable dose" of the formulations of the present invention was shown to be unaffected by storage.

The $\Delta^9$ THC of the present invention is pharmaceutically pure. That is, its form is the nonionized resinous drug substance (6aR-trans)-6a,7,8,10a-tetrahydro-6,6,9-trimethyl-3-pentyl-6H-dibenzo[b,d]-pyran-1-ol. Although its preferred embodiment in this invention is not a salt or ester, it will be readily understood by those of skill in the art that other appropriate forms of $\Delta^9$ THC may be synthesized (e.g. esters and salts such as those described in, for example, U.S. Pat. No. 5,847,128 and PCT WO 01/03690, hereby incorporated in their entirety by reference) and thus used in the practice of this invention.

The desired final concentration of $\Delta^9$ THC in a patient's serum will vary from patient to patient depending on, for example, the nature and severity of the condition being treated, and the patient's overall condition, weight, gender and response to the drug, etc. But the desired range will generally be 10–100 ng/ml at 15 minutes following inhalation. The level of $\Delta^9$ THC in a patient's serum can be readily and reliably monitored by gas chromatography/mass spectrophotometry (GC/MS).

The exact treatment protocol to be used may vary from patient to patient depending on the circumstances. For example, in a preferred embodiment of the invention, a patient receiving chemotherapy may have one dose of $\Delta^9$ THC prescribed via inhalation, to be administered 15 minutes before chemotherapy and 4–8 times daily following chemotherapy. In another preferred embodiment, a patient suffering from anorexia associated with AIDS wasting syndrome may have $\Delta^9$ THC by inhalation prescribed 3–5 times daily, 30 minutes before each meal or snack. In other preferred embodiments, a patient suffering form cancer pain, or spasticity related to either multiple sclerosis or spinal cord injury may have $\Delta^9$ THC by inhalation prescribed 3–6 times daily. Those skilled in the art will readily recognize that the treatment protocol may be crafted so as to address the particular needs of each individual patient on a case by case basis.

Figure 2:
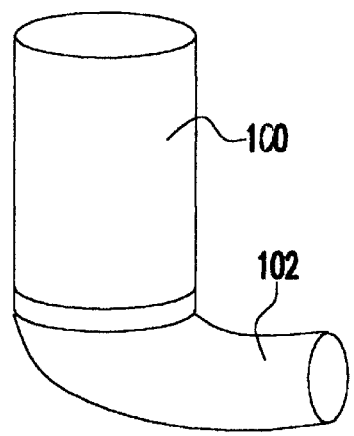
FIG. 2 are generalized schematic drawings of a $\Delta^9$ THC MDI.

$\Delta^9$ THC may be used alone or in combination with other medications. Those skilled in the art will readily recognize that, for example, in the case of AIDS wasting syndrome, the patient will likely also be taking drugs that combat the AIDS virus. Similarly, those skilled in the art will readily recognize that patients receiving chemotherapy for cancer may also receive other antiemetics, and cancer patients seeking to relieve pain are likely to receive opioids as well as nonsteroidal anti-inflammatory agents. The containers for the formulations of the instant invention may be any that are suitable for the efficacious delivery of aerosol inhalants. Several containers and their method of usage are known to those of skill in the art. For example, MDIs can be used with various dose metering chambers, various plastic actuators and mouthpieces, and various aerosol holding chambers (e.g. spacer and reservoir devices), so that appropriate doses of $\Delta^9$ THC reach and deposit in the lung and are thereafter absorbed into the bloodstream. In addition, a lock mechanism such as that shown in U.S. Pat. No. 5,284,133 to Burns and Marshak, which is herein incorporated by reference, can be used to prevent overdose or unauthorized consumption of $\Delta^9$ THC. FIG. 2 provides a generalized drawing of an MDI containing the composition of this invention and provides the advantage of delivering metered quantities of $\Delta^9$ THC on a repetitive basis. The MDI includes a container 100 for holding the composition and a valve delivery mechanism 102 for delivery of aerosolized $\Delta^9$ THC.

IN VIVO EXPERIMENTATION

A $\Delta^9$ THC MDI was formulated and the physical properties of the aerosolized drug characterized. The mass of drug metered by the metering valve was determined following a single actuation (metered dose). The mass of drug delivered (emitted dose) was determined. The mass of particles with an aerodynamic diameter less than 4.7 µm was determined.

Whether inhalation exposure to $\Delta^9$ THC aerosol would elicit pharmacological effects indicative of cannabinoid activity in mice (Compton, D. R., Rice, K. C., De Costa, B. R., Rzdan, R. K., Melvin, L. S., Johnson, M. R., Martin, B. R., Cannabinoid structure-activity relationships: Correlation of receptor binding and in vivo activities, *J Pharmacol Exp Ther*, 265:218–226 (1993); Little et al., 1988) was determined. To assess whether these effects were mediated through a cannabinoid receptor mechanism of action, the specific $CB_1$ receptor antagonist SR 141716A (Rinalidi-Carmona et al., 1994) was used. Blood and brain levels of $\Delta^9$ THC were quantified to provide direct evidence that the drug was absorbed following inhalation exposure. The resulting blood and brain $\Delta^9$ THC concentrations following inhalation exposure were compared to those found following intravenous $\Delta^9$ THC administration using doses of drug that elicited similar antinociceptive effects.

Male ICR mice, weighing approximately 30 g, obtained from Harlan Laboratories (Indianapolis, Ind.) were provided a light cycle of approximately 6 a.m. to 6 p.m., and the temperature remained approximately 23° C. The mice were placed in the lab and allowed to accommodate to the surroundings the evening prior to testing. Animals were allowed food (Harlan Teklab, Madison, Wis.) and water ad libitum.

SR 141716A and $\Delta^9$ THC were obtained from the National Institute on Drug Abuse (Bethesda, Md.). For systemic injections, SR 141716A and $\Delta^9$ THC were dissolved in vehicle, 1:1:18 (ethanol:alkamuls EL-620 (formerly Emulphor EL-620, Rhone-Poluence):saline). Each MDI consisted of a clean, dry, 20 ml plastic coated glass bottle (Wheaton Glass, Milville, N.J.) with a 100 µl inverted metering valve (BK 357, Bespak, Inc., Cary, N.C.). The MDI vehicle consisted of hydrofluoroalkane (HFA) 134a (DuPont, Wilmington, Del.) and ethanol (Aaper Alcohol and Chemical Co., Shelbyville, Ky.). The $\Delta^9$ THC MDIs were prepared using the methods of Byron, 1994 with a formulation that provided a theoretical ex-valve dose of 1 mg $\Delta^9$ THC per 100 µl actuation. Byron, P. R., Dosing reproducibility from experimental albuterol suspension metered-dose inhalers, *Pharm Res*, 11, 580–4 (1994).

Appearance, metered dose reproducibility, emitted dose and particle size distribution of the $\Delta^9$ THC MDI were investigated, before and after storage in an environment maintained at 40° C. and 82% relative humidity for a 28 day period. The mass of drug metered by the metering valve (metered dose, n=10) was determined by collecting single actuations directly from the valve in a puff absorber, using the methods of Byron, 1994. The mass of drug delivered (emitted dose, n=10) was investigated at 28.3 1 min$^{-1}$ using the USP Dosage Sampling Apparatus (USP, Physical Tests and Determinations, <601>, Aerosols, metered-dose inhalers, and dry powder inhalers, in *United States Pharmacopeia*, (USP 24), pp. 1895–1912 (Philadelphia, VA: National Publishing, 2000). Particle size analysis of $\Delta^9$-THC MDI was determined by drawing the samples through an Andersen Cascade Impactor (Andersen Samplers Inc., Atlanta, Ga.) at a volumetric flow rate of 28.3 liter/minute following United States Pharmacopeial guidelines (n=5; USP, 2000). The fine particle dose (n=5), defined as the mass of particles with an aerodynamic diameter less than 4.7 µm, was then determined.

THC was analyzed by LC-UV detection at 280 nm using a 75:25 acetonitrile: 1% acetic acid mobile phase for $\Delta^9$-THC detection. A standard reverse phase C18 column was used. A calibration curve was constructed for each assay based on linear regression of the $\Delta^9$-THC standard peak areas.

The exposure chamber was a modified, inverted, 1-liter separation funnel, housed under a fume hood, which allowed four mice to be simultaneously exposed to the aerosol. Air was drawn through the chamber at a rate of approximately 60 ml/minute and filtered through glass wool (Corning Inc., Corning, N.Y.) and charcoal traps (SKC Inc., Eighty Four, Pa.) upon exiting the exposure chamber. Each actuation of $\Delta^9$-THC or vehicle was delivered once per 5 s and the entire exposure period was 10 min. Mice were exposed to 20, 40 or 60 actuations of aerosolized $\Delta^9$-THC or 60 actuations of vehicle.

Mice were placed in separate clear chambers (16.5 cm×25.5 cm×11.5 cm high) and assessed for hypomotility using a Digiscan Animal Activity Monitor (Omnitech Electronics Inc., Columbus, Ohio) in which the total number of photocell-light beam interruptions was counted. Antinociception was assessed in the tail-flick test (D'Amour, F. E., Smith, D. L., A method for determining loss of pain sensation, *J Pharm Exp Ther*, 72:74–79 (1941)) with heat intensity adjusted to give baseline latencies ranging from 2.0–4.0 seconds. A cut-off time of 10 seconds was used to limit tissue damage. Percent maximum possible effect (%MPE) was determined according to the following formula:

%MPE=[(test latency-baseline latency)/(cut-off-baseline latency)] *100

A ring-test procedure was used to assess catalepsy. The percent of time during a five minute observation period that mice remained motionless, except for movements related to respiration, while stationed on a 5.7 cm diameter ring stand 23 cm above the laboratory bench, was assessed. Body temperature was assessed by inserting a thermometer probe (Traceable Digital, Control Co., Friendswood, Tex.) 2.5 cm into the rectum. Subjects were assessed for baseline tail-flick latency and rectal temperature prior to drug or vehicle administration. In the antagonism studies, mice were given an i.p. injection of SR 141716A or vehicle five-minutes prior to inhalation exposure of aerosols from 60 actuations of either a vehicle or a $\Delta^9$-THC MDI. Locomotor activity, tail-flick latency, catalepsy, and hypothermia were assessed 5, 20, 40, and 60 minutes, respectively, after aerosol exposure. An additional group of animals was given an i.v. injection of $\Delta^9$-THC (0.3, 1, 3, or 10 mg/kg) or vehicle into a lateral tail vein and assessed in the tail-flick test 20 minutes later. All injections were given in a volume of 0.1 ml per 10 g animal weight.

Blood and brain levels of $\Delta^9$-THC were determined as follows. Extraction and LC-MS quantification of $\Delta^9$-THC from whole blood and brain tissue were modified from Lichtman, A. H., Poklis, J. L., Wilson, D. M., Martin, B. R., The pharmacological activity of inhalation exposure to marijuana smoke in mice, *Drug Alc Depend*, 63:107–116 (2001). Particularly, THC and $_2H^3$-THC were extracted from brain material which contains a high degree of lipids. Acetonitrile was added to the pelletized solids and stored in a freezer overnight to separate the acetonitrile layer (which contained THC/$_2H^3$-THC) from the aqueous layers. The following day the acetonitrile layer was removed. In the Lichtman et al., study, 2 ml of 9:1 NaOH was added and the sample was vortexed. Four ml of 9:1 hexane:ethyl acetate was added and the sample was vortexed and spun at 30 rpm for 30 minutes. The vials were then centrifuged at 4,000 rpm at 30 rpm for 10 minutes. The organic layer was removed and evaporated. Upon drying, a derivatizing agent was added and the sample was vortexed, and each sample analyzed by GC/MS. In the present experimentation, the acetonitrile was instead evaporated to dryness under nitrogen. The material was then resolubilized in 0.1 ml methanol. LC-MS identification was used to quantify $\Delta^9$-THC/$_2H^3$-THC in blood and brain matrices. In the present experimentation, calibration standards were prepared from blank mouse whole blood and homogenized brain (2:1, water:brain, v:w). Fifty ng of $^2H_3$-THC (Radian Corporation, Austin, Tex.) was added to the blood sample, brain homogenate, and calibrators as an internal standard. Following an equilibration period, 2.5 ml of cold acetonitrile (HPLC grade, Fisher Scientific, Raleigh, N.C.) was added drop-wise while vortexing. The samples were then centrifuged (Precision Vari-Hi-Speed Centricone, Precision Scientific Co., Chicago, Ill.) at 2500 rpm for 15 minutes to pelletize solids, then stored in the freezer (−20° C.) overnight, allowing the acetonitrile layer to separate from the aqueous layers. The acetonitrile layer was then removed and evaporated to dryness under nitrogen. The $\Delta^9$-THC/$^2H_3$-THC was then resolubilized in 0.1 ml methanol (HPLC grade, Fisher Scientific).

LC-MS identification was used for quantification of $\Delta^9$-THC and $^2H_3$-THC in blood and brain matrices using an 85:15 methanol: 1% glacial acetic acid (0.1% formic acid) mobile phase. A guard column was used inline with the standard reverse phase C18 column. The mass spectrometer was run in APCI+mode. Ions analyzed in single ion monitoring mode were 315 for $\Delta^9$-THC and 318 for $^2H_3$-THC. A calibration curve was constructed for each assay based on linear regression using the peak-area ratios of $\Delta^9$-THC to $^2H_3$-THC of the extracted calibration samples.

The statistical analysis of the data was as follows. Data are represented by means±standard error (s.e.). Statistical analysis of the data was performed using Student t-tests (for the physiochemical comparisons of the aerosol), or ANOVA (for pharmacological studies), with significance set at p<0.05. Post hoc tests for significant ANOVAs included either Dunnett's test or Tukey/Kramer post-hoc analysis. All $ED_{50}$ values were determined using least squares linear regression analysis and calculation of 95% confidence limits (Bliss, C. I., Statistics in Biology (New York: McGraw-Hill, 1967) and were based on the number of actuations of the MDI (i.e., 1 mg/actuation). The Emax for depression of locomotor activity was calculated by double reciprocal plot. The Emax value for percent immobility was assigned the mean from the group that was exposed to 60 mg $\Delta^9$-THC. The Emax values for antinociception and hypothermia were 100% MPE and 6° C. respectively. The $ED_{50}$ of SR 141716A in antagonizing the antinociceptive effects of $\Delta^9$-THC was determined through least squares linear regression analysis and calculation of 95% confidence limits (Bliss, 1967). A sample size of 6–8 mice was used in each group.

Results: THC MDI Physiochemical Characteristics

As shown in Table 5 below, the physiochemical characteristics of the aerosolized $\Delta^9$-THC were unaffected following storage at 40° C. with 82% relative humidity for 28 days. The mass of drug metered by the metering valve following a single actuation was reproducible and unaffected by the accelerated stability storage (p>0.1). There was little variance in the emitted dose and no significant effect of storage (p>0.1). The fine particle dose represented 23.0±0.8% before and 23.6±0.8% after accelerated stability testing of the emitted dose and exhibited no deterioration in $\Delta^9$-THC content (p>0.1).

TABLE 5

Physiochemical characteristics of the $\Delta^9$-THC MDI before and after accelerated stability testing (mean ± s.e.).

| Dose | n | initial evaluation | after 28 days 40° C./82% relative humidity |
|---|---|---|---|
| Metered dose | 10 | 1.10 ± 0.02 | 1.06 ± 0.01 |
| Emitted dose | 10 | 0.90 ± 0.01 | 0.92 ± 0.01 |
| Fine particle dose | 5 | 0.21 ± 0.01 | 0.22 ± 0.01 |

Behavioral evaluation

Having thus determined that the tested MDI delivered a $\Delta^9$-THC aerosol with particles of a sufficiently small mass for lung absorption, further experimentation was conducted to determine whether inhalation exposure to this aerosol could elicit systemic pharmacological effects in mice. Mice exposed to the $\Delta^9$-THC aerosol exhibited cannabinoid activity in each of the four parameters tested (FIGS. 3A–D). Significant effects were found for locomotor inhibition F(3,28)=5.9, p<0.05) (FIG. 3A), antinociception (F(3,28)=7.8, p<0.05) (FIG. 3B), ring immobility (F(3,28)=10.0, p<0.05) (FIG. 3C), and hypothermia (F(3,28)=26.4, p<0.5) (FIG. 3D). The groups exposed to 40 and 60 actuations of $\Delta^9$-THC aerosol significantly differed from vehicle aerosol exposure (Dunnett's test, p<0.05). $ED_{50}$ (95% CL) values were 32 (26–41) mg delivered for locomotor depression, 30 (20–44) mg delivered for antinociception, 30 (22–39) mg delivered for ring immobility, and 33 (25–44) mg of drug delivered for hypothermia.

FIGS. 4A–D show the effect of pretreatment with the specific $CD_1$ receptor antagonist, SR 141716A on the behavioral effects of inhaled $\Delta^9$-THC. Two-way ANOVA revealed that SR 141716A (10 mg/kg) significantly blocked $\Delta^9$-THC-induced hypomotility (F(1,28)=7.4, p<0.05), antinociception (F(1,28)=25.2, p<0.05), catalepsy (F(1,28)=7.4, p<0.05), and hypothermia (F(1,28)=28.9, p<0.05). The groups given a vehicle pretreatment and exposed to the $\Delta^9$-THC aerosol differed from all other groups for each measure (Tukey test, p<0.05).

The dose-response relationship of SR 141716A in antagonizing the antinociceptive effects following exposure to 60 mg of aerosolized $\Delta^9$-THC is shown in FIG. 5. SR 141716A significantly blocked the antinociception, F(5,30)=21.6, p<0.05, with an $AD_{50}$ (95%C.L.) of 0.8 (0.7–1.1 mg/kg).

Table 6 shows the blood and brain $\Delta^9$-THC concentrations, 20 mm after either inhalation exposure to $\Delta^9$-THC aerosol or intraveneous injection of $\Delta^9$-THC. Increasing the amount of drug delivered resulted in increasing concentrations of $\Delta^9$-THC in both matrices. The blood levels of $\Delta^9$-THC following aerosol exposure 20, 40, or 60 mg delivered increased in a dose dependent fashion and were comparable to the blood levels produced by intravenous injection of 3 and 10 mg/kg $\Delta^9$-THC. Brain levels of $\Delta^9$-THC following those exposures were similar to that of 1 and 3 mg/kg intravenous injection of $\Delta^9$-THC. There was dissociation in $\Delta^9$-THC blood and brain concentrations between the inhalation and intravenous routes of administration, an interesting result because other drugs such as methamphetamine, heroin and phencyclidine have been observed to lead to similar brain:blood plasma ratios between the two routes of administration. For the present experimentation, whereas brain levels were 200–300% higher than blood levels following i.v. injection of $\Delta^9$-THC, the brain levels of $\Delta^9$-THC were roughly equivalent to the blood levels of $\Delta^9$-THC following inhalation.

levels of $\Delta^9$-THC at antinociceptive $EC_{50}$ doses for inhalation and i.v. injection of $\Delta^9$-THC as well as comparison of potency ratios between the two routes of administration revealed no significant differences in the different matrices (Table 7).

TABLE 7

Comparison of $\Delta^9$-THC blood and brain concentrations at antinociceptive $ED_{50}$ doses

| Route of Administration | $ED_{50}$ (95% C.L.) | Blood $ED_{50}$ (95% C.L.) | Brain $ED_{50}$ (95% C.L.) |
|---|---|---|---|
| inhalation | 30 (20–44) actuations | 591 (403–866)* | 506 (333–769)* |
| intravenous | 2.4 (1.4–4.2) mg/kg | 230 (102–521) | 604 (270–1350) |

*Potency ratios (95% C.L.) in blood, 1.8 (0.5-4.2), and in brain, 0.6 (0.2–1.5), were not significantly different The HFA 134a-ethanol formulated MDI delivered a respirable $\Delta^9$-THC aerosol in an accurate and reproducible fashion. Preliminary accelerated stability testing revealed that no significant degradation of the $\Delta^9$-THC occurred following storage in extreme conditions. Mice exposed to the aerosol exhibited a full spectrum of pharmacological effects indicative of cannabinoid activity (Compton et al., 1993; Little, P. J., Compton, D. R., Johnson, M. R., Melvin, L. S., Martin, B. R., Pharmacology and stereoselectivity of structurally novel cannabinoids in mice, *J Pharmacol Exp Ther*, 247:1046–1051 (1988)) including hypoactivity, antinociception, catalepsy, and hypothermia. Each of these responses was dose-dependent and antagonized by SR 141716A, indicating a $CB_1$ receptor mechanism of action. The hypothermic effects of $\Delta^9$-THC were not completely antagonized. SR141716A's low $ED_{50}$ (i.e., 0.8 mg/kg) in antagonizing the antinociceptive effects of inhaled $\Delta^9$-THC is in agreement with those of previous reports including exposure to marijuana smoke (0.6 mg/kg; Lichtman et al., 2001), injection of $\Delta^9$-THC (0.4 mg/kg; Compton, D., Aceto, M., Lowe, J., Martin, B., In vivo characterization of a specific cannabinoid receptor antagonist (SR141716A): inhibition of delta-9-tetrahydrocannabinol-induced responses and apparent agonist activity, *J Pharmacol Exp Ther*, 277, 586–594 (1996)), or injection of the synthetic cannabinoid WIN 55,212-2 (1.6 mg/kg; Rinaldi-Carmona, M., Barth, F., Heaulme, M., Shire, D., Calandra, B., Congy, C., Martinez, S., Maruani, J., Neliat, G., Caput, D., Ferrara, P., Sotibrie, P., Breliere, J. C., Le Fur, G., SR141716A, a potent and selective antagonist of the brain cannabinoid receptor, *FEBS Lett*, 350:240-244 (1994)).

Antinociceptive effect and blood and brain concentrations of $\Delta^9$-THC 20 min after treatment

| route of administration | THC dose | % MPE (mean ± S.E.) | ng $\Delta^9$-THC/g blood (mean ± S.E.) | ng $\Delta^9$-THC/g brain (mean ± S.E.) |
|---|---|---|---|---|
| inhalation | 20 actuations | 37 ± 11* | 409 ± 86 | 340 ± 36 |
| | 40 actuations | 58 ± 14* | 788 ± 273 | 791 ± 94 |
| | 60 actuations | 78 ± 11* | 1132 ± 240 | 890 ± 151 |
| intravenous | 1 mg/kg | 31 ± 8 | 102 ± 6 | 307 ± 28 |
| | 3 mg/kg | 70 ± 14 | 365 ± 39 | 854 ± 42 |
| | 10 mg/kg | 67 ± 11 | 1324 ± 38 | 3307 ± 190 |

Figure 3B:
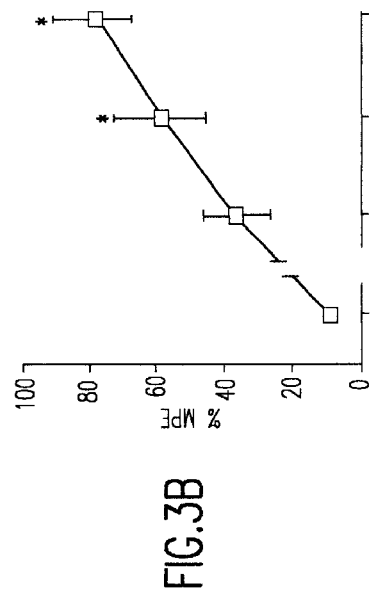
FIGS. 3A–3D are graphs reflecting cannabinoid activity parameters (locomotor activity, %immobility, %MPE, temperature) for mice exposed to $\Delta^9$-THC aerosol according to the invention.
Figure 3A:
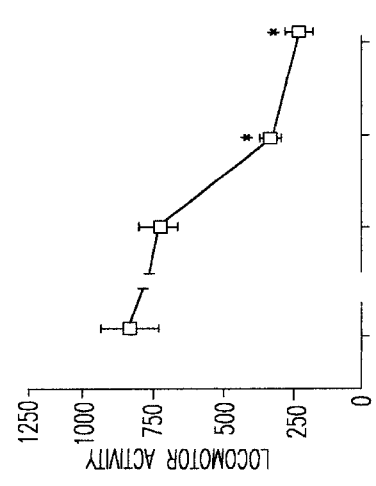
Figure 3D:
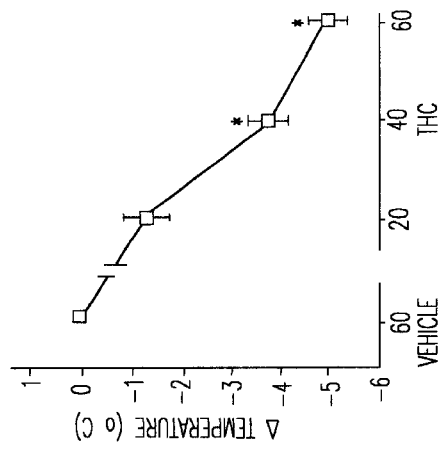
Figure 3C:
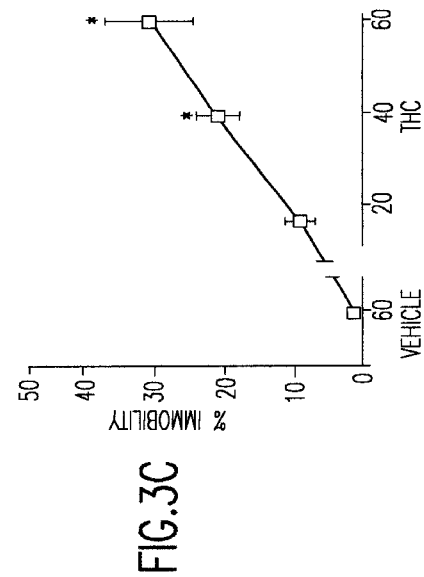

*From FIG. 3B

Comparison of MDI antinociceptive potency with blood and brain concentrations of $\Delta^9$-THC resulted in a high correlation ($r^2=0.997$ and $r^2=0.889$ for blood and brain, respectively). Additionally, comparison of blood and brain Unlike parenteral methods of delivery in which a known amount of drug is injected, determining the absorbed dose of an inhaled drug is difficult to quantify. Although a large mass of drug was actuated into the inhalation chamber, the majorgeneral ity of drug mass is lost because it either deposits on the exposure apparatus or escapes with exhausted air out of the apparatus. Additionally, physiological properties, such as tidal volume and respiratory rate, influence drug inhalation. Finally, because mice are obligate nasal breathers, many particles do not reach the lungs. Therefore, for the above experimentation, dose was indirectly assessed by comparing the concentration of $\Delta^9$-THC in whole blood and brain after inhalation and i.v. routes of adminstration. For both routes of administration, the concentrations of drug increased in both matrices with increasing doses. Inhalation exposure of each respective dose of aerosolized $\Delta^9$-THC resulted in equivalent concentrations of the parent compound in blood and brain. On the other hand, i.v. administration resulted in $\Delta^9$-THC brain levels that were approximately two to three fold higher than those found in blood. The $EC_{50}$ values for inhalation exposure and i.v. injection in the above experimentation were not significantly different in either matrix. Consequently, exposure to the $\Delta^9$-THC aerosol produced dose-dependent increases of $\Delta^9$-THC in blood and brain levels, and the levels necessary to produce cannabinoid behavioral effects were similar to i.v. injection.

In applying the results of the above experimentation on mice to other animals, it will be taken into account that mice are obligate nose-breathers with an extensive nasal infra-architecture, such that substantial nasal deposition may have hindered alveoli deposition. Schlesinger (1985) reported upper respiratory tract deposition of particle sizes between 2–3 $\mu$m ranged from 20–40%. Schlesinger, R. B., Comparative deposition of inhaled aerosols in experimental animals and humans: a review, *J Toxicol Environ Health*, 15:197–214 (1985). Using empirical modeling, Asgharian et al. (1995) calculated that less than 15% of particles with a mass median aerodynamic diameter of 2–3 $\mu$m could reach the alveolar regions of rats compared to a 40% value in humans, and this percentage would be expected to be even lower in mice because of the smaller respiratory tract and general anatomical differences between rats and mice. Asgharian, B., Wood, R., Schlesinger, R. B., Empirical modeling of particle deposition in the alveolar region of the lungs: A basis for interspecies extrapolation, *Fund Appl Toxicol*, 27, 232–238 (1995). Consequently, a considerable amount of the exposed dose is likely to have been deposited in the upper respiratory tract of the mice. In addition, such impacted particles could be moved to the throat, via ciliary action, and swallowed, resulting in gastrointestinal absorption. However, such absorption would not be expected to be as rapid as alveolar absorption. Hence, this delayed absorption might act to maintain $\Delta^9$-THC blood and brain levels for a prolonged period of time. Despite-the extensive filtering done by mice, the fine particle dose generated by the MDI (i.e., 0.22 mg per actuation) was sufficient to result in the rapid elicitation of pharmacological behavior suggesting that the behavioral effects were due to absorption in either the lungs or the upper respiratory tract and not due to gastrointestinal absorption. Nonetheless, nasal filtering is of little concern in humans and the fact that locomotor depression occurred within 5 minutes of exposure and antinociception occurred at 20 minutes is consistent with the notion that a sufficient amount of the aerosol reached the lungs.

The results of Tables 5–7 and FIGS. 3A–5 are particularly significant because of the difficulties of exploiting properties of, and effectively delivering, $\Delta^9$-THC. For example, cannabinoid activity in mice has been reported following exposure to marijuana smoke; however, placebo smoke mimicked marijuana in hypothermia and locomotor inhibition assays. Lichtman et al., 2001. Moreover, in the Lichtman et al. study, SR 141716A only effectively antagonized the antinociceptive response, raising concerns that exposure to the other chemicals in burned marijuana besides $\Delta^9$-THC, as well as possible effects of a hypoxic state, were of consequence there. These other chemicals may have unwanted and unexpected interactions with other drugs. Thus, delivering $\Delta^9$-THC without all the other chemicals of marijuana is highly advantageous. However, such $\Delta^9$-THC delivery has not been easily provided. The behavioral effects of a $\Delta^9$-THC aerosol generated by a nebulizer have been reported, A. H. Lichtman, J. Peart, J. L. Poklis, D. T. Bridgen, R. Z. Razdan, D. M. Wilson, A. Poklis, Y. Meng, P. R. Byron, B. R. Martin, "Pharmacological evaluation of aerosolized cannabinoids in mice," Eur. J. Pharmacol. 399:141–149 (2000). While this method for exposing mice to a $\Delta^9$-THC aerosol removed the confounding influence of smoke, the only cannabinoid behavior observed was a moderate degree of antinociception. Although separation of the potentially therapeutic effects, such as antinociception, from the other pharmacological effects of $\Delta^9$-THC is a desirable goal, the modest cannabinoid effect was attributed to the relatively low blood levels of $\Delta^9$-THC. A 10-minute exposure to the nebulized aerosol resulted in a drug blood concentration of approximately 100 ng $\Delta^9$-THC/ml blood, whereas the $\Delta^9$-THC blood levels of mice following a 10 minute exposure to 20 actuations of the MDI aerosol was around 400 ng/g blood. (Table 8.) Another problem with using the nebulizer to deliver aerosolized $\Delta^9$-THC is the vehicle for dissolution of $\Delta^9$-THC, with some surfactants (such as Emulphor) not having FDA approval for inhalation exposure in humans.

TABLE 8

$\Delta^9$-THC blood levels in mice

| Administration | $\Delta^9$-THC blood level (ng $\Delta^9$-THC/ml blood) |
| --- | --- |
| Nebulized aerosol* | 100 |
| MDI aerosol** (20 actuations) | 400 |

*Emulphor as the surfactant
**Ethanol cosolvent; HFA 134a propellant

Other advantages of $\Delta^9$-THC delivery according to the present invention also are seen. The present invention delivers a systemic dose of $\Delta^9$-THC via the lungs. The development of a $\Delta^9$-THC MDI, which leads to-a rapid onset of action, consistent blood levels, and by-passing the first-pass metabolism in the liver, suggests the viability of the $\Delta^9$-THC aerosol as a replacement for oral $\Delta^9$-THC.

In sum, the experimentation discussed above with regard to Tables 5–7 and FIGS. 3A–5 show, inter alia, that a $\Delta^9$-THC MDI was formulated that can be used to provide a systemic dose of $\Delta^9$-THC via the lungs, and that a $\Delta^9$ THC MDI is capable of producing the full constellation of cannabinoid effects in mice. Physiochemical characteristics of the aerosol were assessed before and after accelerated stability testing. Following this characterization, mice were exposed to the aerosol and evaluated for pharmacological effects indicative of cannabinoid activity, including hypomotility, antinociception, catalepsy, and hypothermia. The $CB_1$ receptor antagonist SR 141716A was used to determine whether the pharmacological effects were mediated by the cannabinoid receptor. The fine particle does of $\Delta^9$ THC was 0.22±0.03 mg (mean±S.D.) or 25% of the emitted dose. In addition, the physiochemical properties of the aerosol were unaffected by accelerated stability testing. A 10-minute exposure to aerosolized $\Delta^9$ THC elicited hypomotility, antinociception, catalepsy, and hypothermia. Additionally, $\Delta^9$ THC concentrations in blood and brain at the antinociceptive $ED_{50}$ dose were similar for both inhalation and intravenous routes of administration. Finally, pretreatment with 10 mg/kg (i.p.) of SR 141716A significantly antagonized all of the $\Delta^9$ THC-induced effects. These results indicate that an MDI is a viable method to deliver a systemic dose of $\Delta^9$ THC that elicits a full spectrum of cannabinoid pharmacological effects in mice that is mediated via a $CB_1$ receptor mechanism of action.

The experimental findings set forth herein suggest that an aerosolized form of $\Delta^9$-THC for medicinal use may be provided. Dosages for mice have been provided, and typically human doses are about 100 times lower than mouse doses on a mg/kg basis. The demonstration that a $\Delta^9$-THC aerosol, generated by a MDI, is relatively stable and produces systemic pharmacological effects in mice has clinical applications in the treatment of many disorders, including pain management as well as the indications for orally-available $\Delta^9$-THC. The availability of a highly reproducible $\Delta^9$-THC aerosol, without exposure to potentially harmful chemicals and carcinogens present in marijuana smoke, is particularly advantageous for the treatment of human patients.

While in the present invention use of $\Delta^9$ THC (see FIG. 7A) is particularly preferred, it will be appreciated that in place of $\Delta^9$ THC may be used $\Delta^9$ THC derivatives and substitutes, e.g., $\Delta^8$ THC (FIG. 7B), 11 hydroxy $\Delta^9$-THC (FIG. 7C), cannabinol (CBN) (FIG. 7D), cannabidiol (CBD) (FIG. 7E); synthetic cannabinoids (such as nabilone (FIG. 7F), levonantradol (FIG. 7G), (–)-HU-210 (FIG. 7H), Win 55212-2 (FIG. 7I)); Anandamide (FIG. 7J), Methandamine (FIG. 7K), CP 55940 (FIG. 7L), O-1057 (FIG. 7M), SR141716A (FIG. FIG. 7N).

While the invention has been described in terms of its preferred embodiments, those skilled in the art will recognize that the invention can be practiced with modification within the spirit and scope of the appended claims.

We claim:

1. A method of administering a pharmaceutically effective dose of aerosolized $\Delta^9$ tetrahydrocannabinol to a patient, comprising the steps of:
   providing a solution comprising a pharmaceutically acceptable form of $\Delta^9$ tetrahydrocannabinol (THC) in a hydrofluoroalkane, said solution having not more than 15% w/w of a pharmaceutically acceptable solvent;
   aerosolizing the THC solution to provide respirable droplets comprising THC wherein at least 20% of the mass of the respirable droplets comprise droplets having an aerodynamic diameter of less than 5.8 µm;
   administering a pharmaceutically effective does of said respirable droplets to a patient's lungs.

2. A method of administering a pharmaceutically effective dose of aerosolized $\Delta^9$ tetrahydrocannabinol to a patient, comprising the steps of:
   providing a solution comprising a pharmaceutically acceptable form of tetrahydrocannabinol (THC) in a hydrofluoroalkane, said solution having not more than 15% w/w of a pharmaceutically acceptable solvent;
   aerosolizing the solution to provide respirable droplets comprising THC wherein at least 20% of the mass of the respirable droplets comprise droplets having an aerodynamic diameter of less than 5.8 µm;
   administering a pharmaceutically effective dose of said respirable droplets to a patient's lungs to achieve brain levels of THC that are substantially the same as blood levels of THC in said patient.

3. The method of claim 2 wherein said solution comprises less than 15% w/w of a solvent selected from the group consisting of ethanol, propanol, propylene glycol, glycerol, and polyethylene glycol.

4. The method of claim 3 wherein said solvent comprises ethanol.

5. The method of claim 1 wherein said solution consists essentially of a hydrofluoroalkane propellant and $\Delta^9$-tetrahydrocannabinol.

6. The method of claim 1 wherein said pharmaceutically effective dose is sufficient to reduce nausea.

7. The method of claim 1 wherein said pharmaceutically effective dose is sufficient to reduce vomiting.

8. The method of claim 1 wherein said pharmaceutically effective dose is sufficient to reduce pain.

9. The method of claim 1 wherein said pharmaceutically effective dose is sufficient to relieve muscle spasticity.

10. The method of claim 1 wherein said pharmaceutically effective dose is sufficient to relieve migraine headaches.

11. The method of claim 1 wherein said pharmaceutically effective dose is sufficient to relieve movement disorders.

12. The method of claim 1 wherein said pharmaceutically effective dose is sufficient to increase appetite in patients suffering from cachexia.

13. The method of claim 2 wherein said pharmaceutically acceptable form of THC is pure $\Delta^9$-tetrahydrocannabinol and said hydrocannabinol is selected from the group consisting of hydrofluoroalkane (HFA) 134a and HFA 227.

14. The method of claim 2 wherein the droplets are less than about 10 µm.

15. A method according to claim 1 wherein the pharmaceutically effective dose is effective to achieve a serum concentration level in a patient of 10–100 ng/ml fifteen minutes following inhalation.

16. A method according to claim 1 comprising a pharmaceutically acceptable salt of $\Delta^9$-tetrahydrocannabinol.

* * * * *